United States Patent
Zhuang et al.

(10) Patent No.: US 11,467,166 B2
(45) Date of Patent: Oct. 11, 2022

(54) COMPOSITIONS AND METHODS FOR DETECTING MOLECULE-MOLECULE INTERACTIONS

(71) Applicant: ShanghaiTech University, Pudong New Area (CN)

(72) Inventors: Min Zhuang, Shanghai (CN); Haopeng Wang, Shanghai (CN); Qiang Liu, Shanghai (CN)

(73) Assignee: ShanghaiTech University, Shanghai (CN)

( * ) Notice: Subject to any disclaimer, the term of this patent is extended or adjusted under 35 U.S.C. 154(b) by 351 days.

(21) Appl. No.: 16/756,464

(22) PCT Filed: Oct. 23, 2018

(86) PCT No.: PCT/CN2018/111385
§ 371 (c)(1),
(2) Date: Apr. 15, 2020

(87) PCT Pub. No.: WO2019/080829
PCT Pub. Date: May 2, 2019

(65) Prior Publication Data
US 2021/0199665 A1 Jul. 1, 2021

(30) Foreign Application Priority Data
Oct. 23, 2017 (WO) ................ PCT/CN2017/107356

(51) Int. Cl.
*G01N 33/68* (2006.01)
*C12N 9/00* (2006.01)

(52) U.S. Cl.
CPC ........... *G01N 33/6845* (2013.01); *C12N 9/93* (2013.01); *C07K 2319/03* (2013.01); *C07K 2319/70* (2013.01); *G01N 2333/9015* (2013.01)

(58) Field of Classification Search
None
See application file for complete search history.

(56) References Cited

U.S. PATENT DOCUMENTS

2010/0055715 A1   3/2010   Pearce et al.

FOREIGN PATENT DOCUMENTS

| WO | WO 20131144656 A1 | 10/2013 |
| WO | WO 2013166234 A1 | 11/2013 |

OTHER PUBLICATIONS

Kyle J. Roux et al. "A promiscuous biotin ligase fusion protein identifies proximal and ineracting proteins in mammalian cells" The Journal of Cell Biology, vol. 196, No. 6, Mar. 19, 2012 (Mar. 19, 2012), the whole document.
International Search Report in PCT Application No. PCT/CN2018/111385 dated Jan. 25, 2019.

*Primary Examiner* — Kagnew H Gebreyesus
(74) *Attorney, Agent, or Firm* — Sheppard Mullin Richter & Hampton LLP

(57) ABSTRACT

Compositions and methods for detecting molecule-molecule interactions are provided. The methods employ a prokaryotic ubiquitin-like protein (Pup) and a Pup ligase that is coupled to one of the molecules. When the Pup ligase is brought to proximity to the other molecule by virtue of the molecule-molecule interaction, the Pup ligase can conjugate the Pup to a lysine residue on the other molecule. As such conjugation can be easily detected, this method allows easy identification of the molecule-molecule interaction.

17 Claims, 21 Drawing Sheets
Specification includes a Sequence Listing.

COMPOSITIONS AND METHODS FOR DETECTING MOLECULE-MOLECULE INTERACTIONS

CROSS-REFERENCE TO RELATED PATENT APPLICATIONS

This application is a U.S. National Stage Application under 35 U.S.C. 371 of International Application No. PCT/CN2018/111385, file Oct. 23, 2018, which claims priority to PCT/CN2017/107356, filed on Oct. 23, 2017, the contents of all of which are incorporated herein by reference in their entirety in the present disclosure.

BACKGROUND

Transmembrane and membrane-tethered proteins make up more than 30% of the human proteome and are important for cellular communication as well as organelle organization. Communication between cells is often controlled by the interaction of membrane proteins, and most signaling pathways are initiated by the engagement of cell surface receptors.

It has been challenging to study membrane-membrane protein interactions using traditional affinity pull down coupled with mass spectrometry characterization. This is partly due to the hydrophobic characteristic of trans-membrane regions of membrane protein, the harsh membrane protein extraction conditions that disrupt protein interactions, as well as transient and weak interactions between membrane receptors and their downstream signaling proteins. In addition, membrane lipid-assisted protein-protein interactions are largely missed in affinity pull down experiments due to the loss of intact lipid bilayers.

A few hybrid-based technologies have been developed to characterize membrane PPIs, including MYTH (split-ubiquitin membrane yeast two-hybrid) and MAPPIT (mammalian protein-protein interaction trap), the latter using either a split protein or a kinase coupled to a transcriptional activation of a marker gene for protein-protein interaction (PPI) readout. All these methods, however, depend on generations of a biased prey library, which is unlikely to cover the whole human proteome. A library-free method is therefore urgently needed to cover a wider spectrum of the human proteome.

More recently, proximity tagging systems such as BioID and APEX have been used to identify PPIs. With these methods, the protein of interest (bait) is genetically fused to one of the proximity labeling enzymes. In the presence of biotin-containing substrates, the fused enzyme will activate and release the activated substrates. While diffusing away from the enzyme, the activated substrates react with proximal proteins, leaving a biotin tag on the target protein. The rationale for PPI study is that the interacting proteins are in close proximity to the bait and thus they will be more likely labeled with the proximity enzyme. These proximity enzymes, mostly engineered ligase or peroxidase, have various tagging radius' and perhaps works best in a confined compartment as shown before. When proximity tagging is used to study PPI in an open compartment, the method is usually combined with quantitative mass spectrometry to differentiate binding partners from background labeling.

Another type of proximity tagging is NEDDylator which hijacks the NEDDylation pathway in mammalian cells by fusing a NEDD8-conjugating enzyme to the bait protein, then labeling the prey with NEDD8, an ubiquitin-like protein. The activated NEDD8 covalently links to the enzyme and waits for a lysine attack from the prey protein, significantly reducing the background. The NEDDylator approach is less orthogonal since the endogenous NEDD8 pathway is important in cell cycle control, proliferation, DNA damage repair, etc.

SUMMARY

The present disclosure, in some embodiments, relates to a proximity tagging system referred to as PUP-IT (Puplyation-based Interacting Tagging). The PUP-IT system takes advantage of the Pup bacteria protein-conjugating system, and employs PafA, a Pup ligase, fused, conjugated or otherwise coupled to the bait protein. Pup is a small bacteria protein that carries about 64 amino acids with Gly-Gly-Gln at the C-terminus. The C-terminus Gln is deaminated to Glu (this form of Pup will be referred as Pup(E)). In the presence of ATP, Pup ligase PafA catalyzes the phosphorylation of the Pup(E) C-terminus Glu, which in turn conjugates the C-terminus Glu to a lysine residue side chain on the target protein. Since lysine is present in most human proteins, by coupling a PafA to a protein of interest, PafA may also ligate Pup(E) to nearby lysines on the fused protein (bait) as well as any proteins (prey) that are interacting with the bait.

In accordance with one embodiment of the present disclosure, therefore, provided is method of detecting binding between a protein having at least a lysine residue and a molecule, comprising: incubating a sample that comprises (a) a prokaryotic ubiquitin-like protein (Pup), (b) the protein, and (c) the molecule coupled to a Pup ligase, under conditions to allow the protein to bind the molecule, thereby allowing the Pup ligase to conjugate the Pup to the lysine residue of the protein; and detecting the conjugation of the Pup to the protein which indicates binding between the protein and the molecule.

In some embodiments, the molecule is a second protein, a small molecule drug, a hormone, a lipid or a polysaccharide. In some embodiments, the Pup ligase is conjugated to the molecule. In some embodiments, the Pup ligase is coupled to the molecule through a pair of proteins capable of binding each other. In some embodiments, the binding is chemically induced dimerization (CID). In some embodiments, the molecule is a second protein and the Pup ligase is fused to the molecule.

In some embodiments, the binding is through hydrophobic interaction, electro statistic interaction, or hydrogen bond. In some embodiments, at least one of the protein and the molecule is a membrane-bound or transmembrane protein. In some embodiments, the protein is present on the surface of a first cell and the molecule is present on a second cell. In some embodiments, the first cell is a tumor cell and the second cell is a CAR-T cell or vice versa.

In another embodiment, the present disclosure provides a method of coupling a molecule to a protein having at least a lysine residue, comprising contacting the protein with (a) the molecule coupled to a prokaryotic ubiquitin-like protein (Pup) in the presence of (b) a Pup ligase coupled to a second protein capable of binding the protein, under conditions to allow the second protein to bind the protein thereby enabling the Pup ligase to conjugate the Pup to the lysine residue, thereby coupling the molecule to the protein.

In some embodiments, the protein is an antibody. In some embodiments, the second protein is protein G or an antibody having specificity to the Fc fragment of the antibody. In some embodiments, the molecule is selected from the group consisting of a small molecule drug, a detectable label, a nucleotide, a protein, and combinations thereof.

Yet in another embodiment, a kit or package is provided, comprising a prokaryotic ubiquitin-like protein (Pup) and a bait protein coupled to a Pup ligase, wherein the Pup ligase is capable of conjugating the Pup to a lysine residue of a protein.

Also provided, in one embodiment, is a complex comprising a prokaryotic ubiquitin-like protein (Pup) ligase coupled to a transmembrane protein. In some embodiments, the Pup ligase is fused to the intracellular terminus of the protein. In some embodiments, the Pup ligase is fewer than 20 amino acid residues away from the intracellular terminus of the protein.

Yet another embodiment provides an isolated cell comprising the complex of any of the above embodiments on the cell membrane. In some embodiments, provided is a recombinant protein comprising a prokaryotic ubiquitin-like protein (Pup) ligase and a dimerizing protein. In some embodiments, the dimerizing protein is selected from the group consisting of FKBP, CalcineurinA (CNA), CyP-Fas, FRB domain of mTOR, GyrB, GAI, GID1, Snap-tag, HaloTag, and eDHFR.

DETAILED DESCRIPTION

Definitions

Figure 1A:
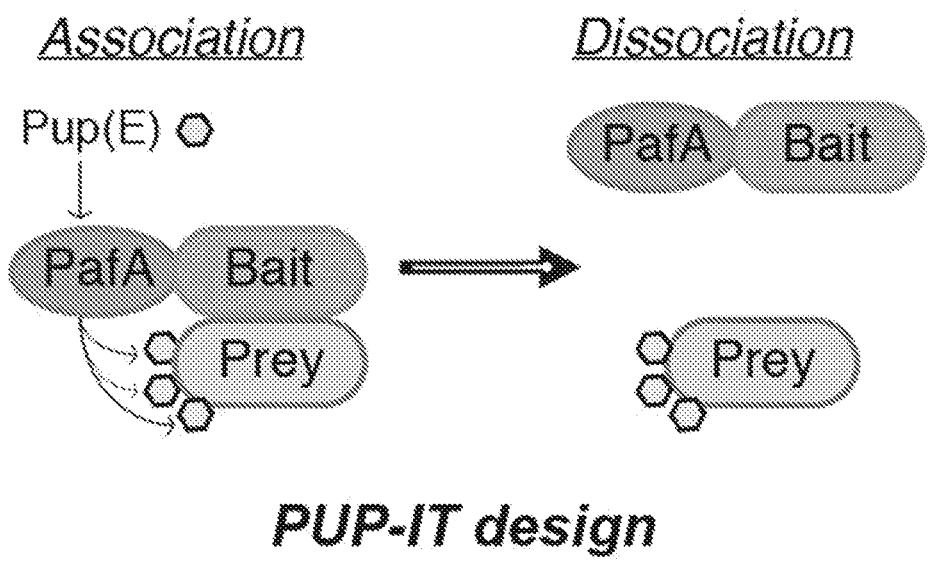
FIG. 1a-f illustrate the design and validation of PUP-IT proximity tagging system according to one embodiment of the disclosure. (a) Schematic view of PUP-IT design. PafA (green) is genetically fused to bait protein (orange) and mediates Pup(E) (yellow) modification of prey protein (blue). Covalent Pup modification preserves even when bait and prey proteins dissociate. (b) Sequence alignment of all known PafA modification sites revealed no specific primary sequence context for lysine modification. The alignment is generated with WebLogo. (c) Terminal fusion of other proteins do not affect PafA enzymatic activity. PafA is either fused to the C terminus of GST or the N terminus of XIAP, both proteins are randomly selected. In the presence of ATP and Pup(E) protein, both GST-PafA and PafA-XIAP are modified with multiple Pup(E) in a coomassie stained SDS-PAGE. (d) The Pup(E) modification sites on GST are evenly distributed on protein surface. The GST dimer is shown in green and cyan while the modified lysines are highlighted in purple. Similar result is observed with PafA-XIAP. (e) The modification of GST is dependent on the direct connection between GST and PafA enzyme. In vitro pupylation assays are set up with purified recombinant GST-PafA or GST with free PafA with increased concentration. (f) The N terminus of Pup(E) can be modified. In vitro pupylation assays are set up with either sPup(E) (a truncated short version of Pup, amino acids 37-64), unmodified Pup(E) or GST-Pup(E). Similar modification can be observed.

It is to be noted that the term "a" or "an" entity refers to one or more of that entity; for example, "an antibody," is understood to represent one or more antibodies. As such, the terms "a" (or "an"), "one or more," and "at least one" can be used interchangeably herein.

As used herein, the term "polypeptide" is intended to encompass a singular "polypeptide" as well as plural "polypeptides," and refers to a molecule composed of monomers (amino acids) linearly linked by amide bonds (also known as peptide bonds). The term "polypeptide" refers to any chain or chains of two or more amino acids, and does not refer to a specific length of the product. Thus, peptides, dipeptides, tripeptides, oligopeptides, "protein," "amino acid chain," or any other term used to refer to a chain or chains of two or more amino acids, are included within the definition of "polypeptide," and the term "polypeptide" may be used instead of, or interchangeably with any of these terms. The term "polypeptide" is also intended to refer to the products of post-expression modifications of the polypeptide, including without limitation glycosylation, acetylation, phosphorylation, amidation, derivatization by known protecting/blocking groups, proteolytic cleavage, or modification by non-naturally occurring amino acids. A polypeptide may be derived from a natural biological source or produced by recombinant technology, but is not necessarily translated from a designated nucleic acid sequence. It may be generated in any manner, including by chemical synthesis.

The term "isolated" as used herein with respect to cells, nucleic acids, such as DNA or RNA, refers to molecules separated from other DNAs or RNAs, respectively, that are present in the natural source of the macromolecule. The term "isolated" as used herein also refers to a nucleic acid or peptide that is substantially free of cellular material, viral material, or culture medium when produced by recombinant DNA techniques, or chemical precursors or other chemicals when chemically synthesized. Moreover, an "isolated nucleic acid" is meant to include nucleic acid fragments which are not naturally occurring as fragments and would not be found in the natural state. The term "isolated" is also used herein to refer to cells or polypeptides which are isolated from other cellular proteins or tissues. Isolated polypeptides is meant to encompass both purified and recombinant polypeptides.

As used herein, the term "recombinant" as it pertains to polypeptides or polynucleotides intends a form of the polypeptide or polynucleotide that does not exist naturally, a non-limiting example of which can be created by combining polynucleotides or polypeptides that would not normally occur together.

Methods of Detecting Molecule-Molecule Interactions

On embodiment of the present disclosure provides methods for detecting molecule-molecule interactions. A new proximity tagging system named PUP-IT (Puplyation-based Interacting Tagging) is hereby developed by the instant inventors. PafA is a prokaryotic ubiquitin-like protein (Pup) ligase in the Pup bacteria protein-conjugating system. Pup is a small bacteria protein that carries about 64 amino acids with Gly-Gly-Gln at the C-terminus. When the C-terminus Gln is deaminated to Glu (this form of Pup will be referred to as Pup(E)), in the presence of ATP, Pup ligase PafA can catalyze the phosphorylation of the Pup(E) C-terminus Glu, which in turn conjugates the C-terminus Glu to a lysine residue side chain on the target protein.

Therefore, in the presence of a Pup, if the PafA is coupled to a molecule that can bring the PafA into proximity to a lysine-containing protein by virtue of binding between the molecule and the protein, the PafA can then conjugate the Pup to the lysine residue of the protein. By detection of the Pup conjugation, the binding between the molecule and the protein can be determined. As such a binding does not need to be strong to bring together the PafA and the lysine-containing protein, such a process can be useful for detecting even very weak molecule-molecule interactions.

In accordance with one embodiment of the present disclosure, therefore, provided is a method for detecting binding between a protein having at least a lysine residue and a molecule. In one embodiment, the method entails incubating a sample that comprises (a) a prokaryotic ubiquitin-like protein (Pup), (b) the protein (also referred to as a "prey"), and (c) the molecule (also referred to as a "bait") coupled to a Pup ligase, under conditions to allow the protein to bind the molecule. If the bait can bind to the prey, then binding will bring the Pup ligase in proximity to the prey. Since the Pup is present in the sample, the Pup ligase will be able to conjugate the Pup to the lysine of the prey. Subsequently, in one embodiment, the method entails detecting the conjugation of the Pup to the protein which indicates binding between the protein and the molecule.

"Prokaryotic ubiquitin-like protein" or "Pup" is a functional analog of ubiquitin found in the prokaryote Mycobacterium tuberculosis. It serves the same function as ubiquitin, although the enzymology of ubiquitylation and pupylation is different. In contrast to the three-step reaction of ubiquitylation, pupylation requires two steps, therefore only two enzymes are involved in pupylation. Similar to ubiquitin, Pup attaches to specific lysine residues of substrate proteins by forming isopeptide bonds. It is then recognized by Mycobacterium proteasomal ATPase (Mpa) by a binding-induced folding mechanism that forms a unique alpha-helix. Mpa then delivers the Pup-substrate to the 20S proteasome by coupling of ATP hydrolysis for proteasomal degradation.

There are an abundance of known Pup proteins, which have well reserved amino acid sequences. For instance, a known Pup protein Superfamily (ID: pfam05639) includes 28 Pup proteins. In addition, Table 1 below lists a number of Pup proteins as well as a truncated one (named "Truncated", SEQ ID NO: 1) which was derived from BAV23336.1 (SEQ ID NO: 2) and tested in the experimental examples.

TABLE 1

Example Pup Proteins

| | |
|---|---|
| BAV23336 | MSVVNAK-QTQIM--GG-GGRDEDNTEDSAQASGQVQINTEGVDSLLDEIDGLLENNAEE |
| Truncated | ------------------------------------------DSLLDEIDGLLENNAEE |
| WP_020934768 | ---MTNP-QSQIS--GG-GDRPEDTNDD-AQGLGQAQVNTAGTDDLLDEIDGLLEENAEE |
| WP_066587666 | MTTGGSG-QGQVH--GGRGRGDGPASGD-VTASGQEQLKVSGTDDLLDEIDGLLESNAEE |
| WP_081106290 | ----------MNA--GG-PNADDDSLDH-SLGTAQAQISATGVDDLLDEIDGLLENNAEE |
| WP_006840328 | -----MA-QQQIH--GG-SGNGSEDEGA--FEAGQAQLNTSGTDDLLDEIDALLDNNAEE |
| WP_066525612 | -----MSNQQQIH--GH-TGGGDDAEGT-PAQAGQAQINTAGTDDLLDEIDALLDTNAEE |
| WP_003845807 | ---MSNK-QSQVQ--GS-GSGDNSDDDD-VQAAGQVQINTTGTDDLLDEIDGLLESNAEE |
| WP_016457481 | -----MA-DKQVY-SSG-GKGPTDDDVV-DGGAGQVQINTHEADSLLDEIDSLLETDSEE |
| WP_076598554 | -----MA-QDQINISGG-GDNGEGEPGD-ARNAGQVNVNTTGTDDLLDEIDALLDTNAEE |
| | |
| BAV23336 | FVRSYVQKGGE (SEQ ID NO: 1) |
| Truncated | FVRSYVQKGGE (SEQ ID NO: 2) |
| WP_020934768 | FVSSYVQKGGQ (SEQ ID NO: 3) |
| WP_066587666 | FVKSYVQKGGQ (SEQ ID NO: 4) |
| WP_081106290 | FVRSYVQKGGQ (SEQ ID NO: 5) |
| WP_006840328 | FVRSYVQKGGE (SEQ ID NO: 6) |
| WP_066525612 | FVRSFVQKGGQ (SEQ ID NO: 7) |
| WP_003845807 | YVSSYVQKGGQ (SEQ ID NO: 8) |
| WP_016457481 | FVKSYVQKGGQ (SEQ ID NO: 9) |
| WP_076598554 | FVRSYVQKGGQ (SEQ ID NO: 10) |

A Pup protein suitable for use with the present technology, therefore, can be any of the Pup proteins disclosed herein, or their truncated forms that includes, e.g., the C-terminal 28 amino acid residues (e.g., SEQ ID NO: 2). In some embodiments, the C-terminal residue can be Glu or modified from another, natural amino acid to Glu.

Suitable Pup proteins can also include biological equivalents of those specifically known or described herein. The term "biological equivalent" of a protein or polypeptide refers to a polypeptide having a certain degree of homology, or sequence identity, with the amino acid sequence of a reference protein or polypeptide. In some aspects, the sequence identity is at least about 70%, 75%, 80%, 85%, 90%, 95%, 98%, or 99%. In some aspects, the equivalent polypeptide or polynucleotide has one, two, three, four or five addition, deletion, substitution and their combinations thereof as compared to the reference protein or polypeptide. In some aspects, the equivalent sequence retains the activity (e.g., conjugating to a lysine) or structure of the reference sequence.

In some embodiments, the amino acid substitution is a conservative amino acid substitution. A "conservative amino acid substitution" is one in which the amino acid residue is replaced with an amino acid residue having a similar side chain. Families of amino acid residues having similar side chains have been defined in the art, including basic side chains (e.g., lysine, arginine, histidine), acidic side chains (e.g., aspartic acid, glutamic acid), uncharged polar side chains (e.g., glycine, asparagine, glutamine, serine, threonine, tyrosine, cysteine), nonpolar side chains (e.g., alanine, valine, leucine, isoleucine, proline, phenylalanine, methionine, tryptophan), beta-branched side chains (e.g., threonine, valine, isoleucine) and aromatic side chains (e.g., tyrosine, phenylalanine, tryptophan, histidine). Thus, a nonessential amino acid residue in an immunoglobulin polypeptide is preferably replaced with another amino acid residue from the same side chain family. In another embodiment, a string of amino acids can be replaced with a structurally similar string that differs in order and/or composition of side chain family members.

Non-limiting examples of conservative amino acid substitutions are provided in the table below, where a similarity score of 0 or higher indicates conservative substitution between the two amino acids.

TABLE 2

Amino Acid Similarity Matrix

| | C | G | P | S | A | T | D | E | N | Q | H | K | R | V | M | I | L | F | Y | W |
|---|---|---|---|---|---|---|---|---|---|---|---|---|---|---|---|---|---|---|---|---|
| W | -8 | -7 | -6 | -2 | -6 | -5 | -7 | -7 | -4 | -5 | -3 | -3 | 2 | -6 | -4 | -5 | -2 | 0 | 0 | 17 |
| Y | 0 | -5 | -5 | -3 | -3 | -3 | -4 | -4 | -2 | -4 | 0 | -4 | -5 | -2 | -2 | -1 | -1 | 7 | 10 | |
| F | -4 | -5 | -5 | -3 | -4 | -3 | -6 | -5 | -4 | -5 | -2 | -5 | -4 | -1 | 0 | 1 | 2 | 9 | | |
| L | -6 | -4 | -3 | -3 | -2 | -2 | -4 | -3 | -3 | -2 | -2 | -3 | -3 | 2 | 4 | 2 | 6 | | | |
| I | -2 | -3 | -2 | -1 | -1 | 0 | -2 | -2 | -2 | -2 | -2 | -2 | -2 | 4 | 2 | 5 | | | | |
| M | -5 | -3 | -2 | -2 | -1 | -1 | -3 | -2 | 0 | -1 | -2 | 0 | 0 | 2 | 6 | | | | | |
| V | -2 | -1 | -1 | -1 | 0 | 0 | -2 | -2 | -2 | -2 | -2 | -2 | -2 | 4 | | | | | | |
| R | -4 | -3 | 0 | 0 | -2 | -1 | -1 | -1 | 0 | 1 | 2 | 3 | 6 | | | | | | | |
| K | -5 | -2 | -1 | 0 | -1 | 0 | 0 | 0 | 1 | 1 | 0 | 5 | | | | | | | | |
| H | -3 | -2 | 0 | -1 | -1 | -1 | 1 | 1 | 2 | 3 | 6 | | | | | | | | | |
| Q | -5 | -1 | 0 | -1 | 0 | -1 | 2 | 2 | 1 | 4 | | | | | | | | | | |
| N | -4 | 0 | -1 | 1 | 0 | 0 | 2 | 1 | 2 | | | | | | | | | | | |
| E | -5 | 0 | -1 | 0 | 0 | 0 | 3 | 4 | | | | | | | | | | | | |
| D | -5 | 1 | -1 | 0 | 0 | 0 | 4 | | | | | | | | | | | | | |
| T | -2 | 0 | 0 | 1 | 1 | 3 | | | | | | | | | | | | | | |
| A | -2 | 1 | 1 | 1 | 2 | | | | | | | | | | | | | | | |
| S | 0 | 1 | 1 | 1 | | | | | | | | | | | | | | | | |
| P | -3 | -1 | 6 | | | | | | | | | | | | | | | | | |
| G | -3 | 5 | | | | | | | | | | | | | | | | | | |
| C | 12 | | | | | | | | | | | | | | | | | | | |

TABLE 3

Conservative Amino Acid Substitutions

| For Amino Acid | Substitution With |
| --- | --- |
| Alanine | D-Ala, Gly, Aib, β-Ala, L-Cys, D-Cys |
| Arginine | D-Arg, Lys, D-Lys, Orn D-Orn |
| Asparagine | D-Asn, Asp, D-Asp, Glu, D-Glu Gln, D-Gln |
| Aspartic Acid | D-Asp, D-Asn, Asn, Glu, D-Glu, Gln, D-Gln |
| Cysteine | D-Cys, S-Me-Cys, Met, D-Met, Thr, D-Thr, L-Ser, D-Ser |
| Glutamine | D-Gln, Asn, D-Asn, Glu, D-Glu, Asp, D-Asp |
| Glutamic Acid | D-Glu, D-Asp, Asp, Asn, D-Asn, Gln, D-Gln |
| Glycine | Ala, D-Ala, Pro, D-Pro, Aib, β-Ala |
| Isoleucine | D-Ile, Val, D-Val, Leu, D-Leu, Met, D-Met |
| Leucine | Val, D-Val, Met, D-Met, D-Ile, D-Leu, Ile |
| Lysine | D-Lys, Arg, D-Arg, Orn, D-Orn |
| Methionine | D-Met, S-Me-Cys, Ile, D-Ile, Leu, D-Leu, Val, D-Val |
| Phenylalanine | D-Phe, Tyr, D-Tyr, His, D-His, Trp, D-Trp |
| Proline | D-Pro |
| Serine | D-Ser, Thr, D-Thr, allo-Thr, L-Cys, D-Cys |
| Threonine | D-Thr, Ser, D-Ser, allo-Thr, Met, D-Met, Val, D-Val |
| Tyrosine | D-Tyr, Phe, D-Phe, His, D-His, Trp, D-Trp |
| Valine | D-Val, Leu, D-Leu, Ile, D-Ile, Met, D-Met |

The term "Pup ligase" or "Pup-protein ligase" refers to a group of proteins which, in the presence of ATP, catalyzes the phosphorylation of the C-terminus Glu of a Pup protein, which in turn conjugates the C-terminus Glu to a lysine residue side chain on a target protein. Pup ligases have well reserved amino acid sequences. Some of the Pup ligases are classified into a GenBank Superfamily (ID: TIGR03686). The Pup ligase tested in the experimental examples here is "Pup-protein ligase [Corynebacterium glutamicum]" (Access No: OKX85684.1), the amino acid sequence of which is listed in the table below.

TABLE 4

Sequence of Pup--protein ligase [*Corynebacterium glutamicum*] (SEQ ID NO: 11)

>OKX85684.1 Pup--protein ligase [*Corynebacterium glutamicum*]
MSTVESALTRRIMGIETEYGLTFVDGDSKKLRPDEIARRMFRPIVEKYSS

SNIFIPNGSRLYLDVGSHPEYATAECDNLTQLINFEKAGDVIADRMAVDA

EESLAKEDIAGQVYLFKNNVDSVGNSYGCHENYLVGRSMPLKALGKRLMP

FLITRQLICGAGRIHHPNPLDKGESFPLGYCVSQRSDHVWEGVSSATTRS

RPIINTRDEPHADSHSYRRLHVIVGDANMAEPSIALKVGSTLLVLEMIEA

DEGLPSLELANDIASIREISRDATGSTLLSLKDGTTMTALQIQQVVFEHA

SKWLEQRPEPEFSGTSNTEMARVLDLWGRMLKAIESGDFSEVDTEIDWVI

KKKLIDRFIQRGNLGLDDPKLAQVDLTYHDIRPGRGLFSVLQSRGMIKRW

TTDEAILAAVDTAPDTTRAHLRGRILKAADTLGVPVTVDWMRHKVNRPEP

QSVELGDPFSAMNSEVDQLIEYMTVHAESYRS

As noted above, once the molecule binds to the protein, the molecule will bring its coupled Pup ligase to the protein. Given that Pup is available in the sample, its C-terminus Glu can be phosphorylated by the Pup ligase which will also conjugate the C-terminus Glu to a lysine residue side chain on the protein.

The protein (the prey) can be any protein that contains at least a lysine or is modified to contain a lysine. The molecule (the bait), on the other hand, can be any molecule as long as it is capable of interacting or binding the protein. Non-limiting examples of molecules include another protein, a small molecule drug, a hormone, a lipid or a polysaccharide.

The molecule can be coupled to the Pup ligase with any methods known in the art, such as conjugation, photoactivable linkage, linkers and binding pairs. In one embodiment, the molecule and the Pup ligase are coupled to each other through a pair of proteins capable of binding each other. One such example is a hormone-receptor pair. Another example is an antigen-antibody pair. Yet another example is a pair of protein for which the binding is chemically induced dimerization (CID). CID is particularly useful as it can be induced by a chemical agent. Examples of CID pairs and dimerizing agents are provided in the table below.

TABLE 5

Chemically induced dimerization pairs

| Target proteins | | Dimerizing agent |
| --- | --- | --- |
| FKBP | FKBP | FK1012 |
| FKBP | CalcineurinA (CNA) | FK506 |
| FKBP | CyP-Fas | FKCsA |
| FKBP | FRB domain of mTOR | Rapamycin |
| GyrB | GyrB | Coumermycin |
| GAI | GID1 | Gibberellin |
| Snap-tag | HaloTag | HaXS |
| eDHFR | HaloTag | TMP-HTag |

In another embodiment, when the molecule is a protein (bait protein), the molecule can be coupled to the Pup ligase through fusion. In the fusion (or chimeric) protein, the bait protein can be placed at the N-terminal or C-terminal end of the Pup ligase. In some embodiments, a spacer is placed between the bait protein and the Pup ligase. The spacer is a short amino acid sequence (e.g., 1-50 amino acids) and can include small amino acids such as glycine and serine.

The presently disclosed technology is able to detect strong, moderately strong or weak molecule-molecule interaction. Weak interactions are typically difficult to detect by existing methods. Some weak interactions are hydrophobic in nature, or through electro statistic interaction or hydrogen bond. In some embodiments, at least one of interacting molecules is a membrane-bound or transmembrane protein. In some embodiments, both molecules are membrane-bound.

Figure 8:
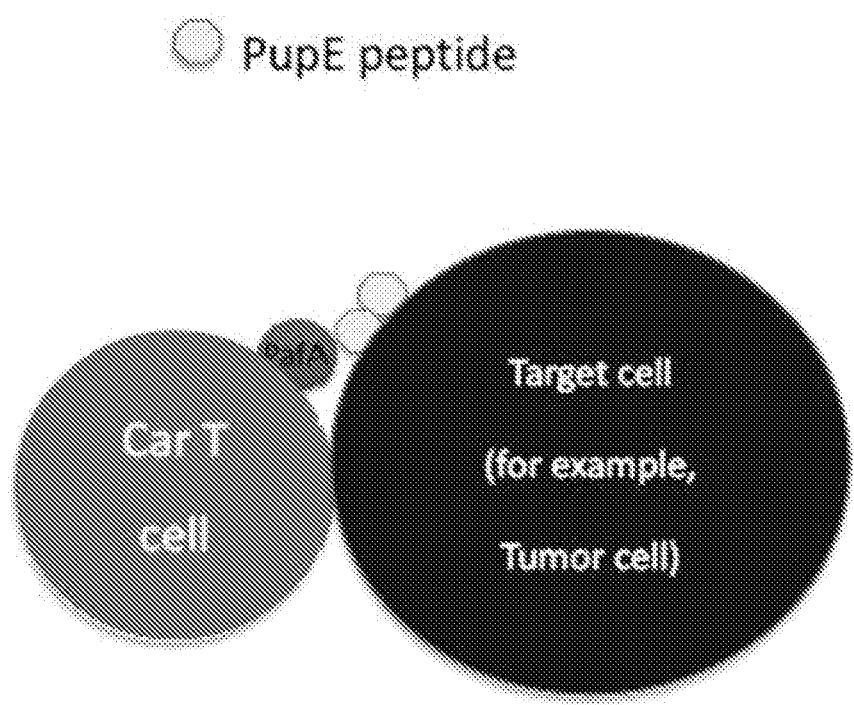
FIG. 8 illustrates the use of PUP-IT to identify binding targets of CAR-T cells.

The present technology can be used to identify target cells of a therapeutic agent, such as a small molecule drug, a protein, or a CAR-T (Chimeric Antigen Receptor (CAR) T-Cell). FIG. 8 illustrates the use of an embodiment of the present disclosure to identify the target cell of a CAR-T cell. A Pup ligase (PafA) can be expressed on the membrane of a CAR-T cell which also expresses certain targeting proteins on the surface. Through these targeting proteins, the CAR-T will bind to a target cell (e.g., a tumor cell), and thereby bringing the PafA into proximity to proteins on the target cell. In the presence of Pup proteins, the PafA will then conjugate the Pup proteins to those proteins on the target cells, effectively labeling the target cell with the Pup proteins. Through detection of the Pup proteins, one can readily show that the target cell has been interacting with the CAR-T cell.

Methods of Coupling a Molecule to a Protein

In some embodiments, the present disclosure also provides methods of coupling molecules to one another, using a Pup as a linker, as long as one of the molecules includes a lysine residue.

In one embodiment, the method entails contacting the lysine-containing protein with (a) the molecule coupled to a prokaryotic ubiquitin-like protein (Pup) in the presence of (b) a Pup ligase coupled to a second protein capable of binding the protein, under conditions to allow the second protein to bind the protein. Once the second protein binds the protein, the Pup ligase will be able to conjugate the Pup to the lysine residue to the protein. Since the Pup is coupled to the molecule, this connects the molecule to the protein. In some embodiments, the molecule is a small molecule drug, a detectable label, a nucleotide, a protein, and combinations thereof.

Figure 7:
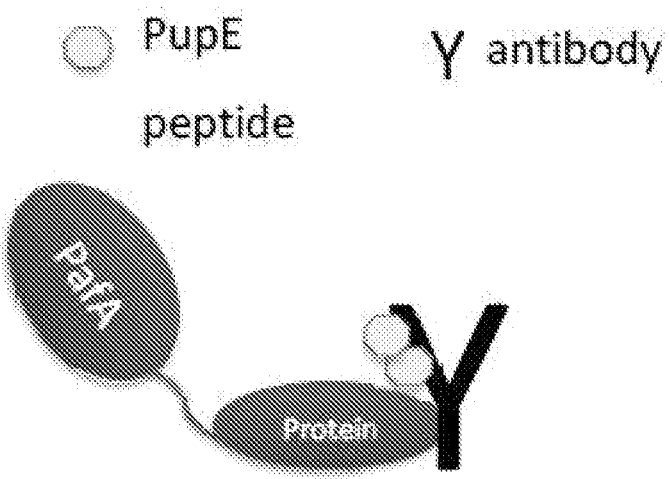
FIG. 7 illustrates the use of PUP-IT in preparing antibody-drug conjugates.

The method is illustrated in FIG. 7, which couples a small molecule drug conjugated to a Pup protein PupE (collectively a hexangular shape) to an antibody (Y shape). In the presence of free antibodies and separate drug-PupE conjugates, a Pup ligase (PafA) fused to a Protein G is added. The Protein G binds to the Fc fragment on the antibody, bringing the PafA to proximity to the antibody, which will then conjugate the drug-PupE to the antibody, making an antibody-drug complex.

Fusion Proteins, Conjugates, Compositions and Kits

Fusion proteins, conjugates, compositions and kits are also provided which are useful for carrying out certain embodiments of the present technology.

In one embodiment, a recombinant fusion protein is provided, which comprises a prokaryotic ubiquitin-like protein (Pup) ligase and a dimerizing protein. A "dimerizing protein" is one of a pair of proteins that are capable of binding each other, in particular when induced with a dimerizing agent. Non-limiting examples of such pairs are provided in Table 5 (chemically induced dimerization pairs).

In one embodiment, the dimerizing protein is selected from the group consisting of FKBP, CalcineurinA (CNA), CyP-Fas, FRB domain of mTOR, GyrB, GAI, GID1, Snaptag, HaloTag, and eDHFR. When another molecule is coupled to the other member of the pair, the dimerization can couple the Pup ligase to the other molecule. This is particularly useful when there is challenges when directly fusing a Pup ligase to a bait molecule.

Also provided, in another embodiment, is a complex comprising a prokaryotic ubiquitin-like protein (Pup) ligase coupled to a transmembrane protein. In one embodiment, the Pup ligase is fused to an extracellular domain or the extracellular terminus of the protein. This can be useful for identifying a binding target (e.g., molecule, cell) for the transmembrane protein.

In another embodiment, the Pup ligase is fused to the intracellular terminus of the protein. Such a fusion protein can be used to identify downstream factor in the cell that interact with the transmembrane protein. In some embodiments, the Pup ligase is fewer than 20 (or alternatively 10, 15, 25, 30, 35, 40, 45, or 50) amino acid residues away from the intracellular terminus of the protein.

Also provided, in one embodiment, are isolated cells comprising the complex on the cell membrane.

Kits and packages are also provided. In one embodiment, the kit or package comprises a prokaryotic ubiquitin-like protein (Pup) and a bait protein coupled to a Pup ligase, wherein the Pup ligase is capable of conjugating the Pup to a lysine residue of a protein. In some embodiments, the kits or package further includes instructions for using the parts in the kit or package.

The present disclosure also provides isolated polynucleotides or nucleic acid molecules encoding the proteins or fusion proteins of the disclosure.

EXAMPLES

Example 1. Tracking Weak Protein-Protein Interactions In and Out Cells Identifies Membrane Receptor Signaling Components This example demonstrates a new method referred to as PUP-IT which specifically tags interacting membrane proteins of interest (MPOI) in cells. This approach transforms transient and weak interactions into covalent bindings, and tagged proteins are enriched by affinity purification under denaturing conditions for mass spectrometry-based identification.

This example applied this approach to CD28, a critical co-stimulatory receptor for T lymphocyte activation. The results identified CD28 binding partners as well as multiple potential interacting proteins. In addition, this example shows that this method can be used to identify the interaction between cell surface receptors and their respective ligands. In conclusion, this example designed a powerful tool to uncover the weak and transient membrane PPIs in cells, which will have a general and broad application in the study of membrane proteins.

Methods and Materials

Molecular Cloning

Corynebacterium glutamicum PafA and Pup cDNA was synthesized by Qinglan Biotech (Wuxi, China) and the sequences were confirmed. Using those synthesized cDNA as the template, we amplified the gene with PCR and cloned them into pGEX6p-1 vector between the restriction enzyme sites Xho1 and Not1 to fuse either PafA or Pup to the C terminus of GST. To generate active Pup(E), quick change was used to mutate the C terminal Q to E. Both PafA-XIAP (1-434) and FRB-PafA were generated with overlapping PCR and cloned between pGEX6p-1 BamH1 and Not1 sites, BamH1 and Sal1 sites respectively. An eight amino acid linker GGSGGGSG (SEQ ID NO: 16) was inserted between PafA and XIAP, while a 17 residue with GGSG repeats was inserted between FRB and PafA. Different PafA-pep fusions were introduced into pGEX6p-1 between BamH1 and Not1. Both GST-MATH (pGEX6p-1-MATH) and His-MATH (pET28a-MATH) fusion vectors are gifts from Caiguang Yang's lab in Shanghai Institute of Materia Medica, Chinese Academy of Science.

For cellular application of PUP-IT, pEF6a is the major backbone plasmid for all transient transfection studies. V5-PafA fused with different MATH binding peptides were cloned into pEF6A between BamH1 and EcoR1 sites with a stop codon added. MATH (residue 28-166 from human SPOP protein) was cloned into pEF6a and fused with the C terminal Myc tag. CD28-PafA, CD28$^{tailless}$ (residues 1-179)-PafA, and CD28$^{544}$ (residues 1-184)-PafA were generated with overlapping PCR and subcloned into pEF6a with Myc tag fused at the C terminus. FKBP was inserted between the N terminal signal peptide (residue 1-19) and mature CD28 (residue 20-220) by overlapping PCR to generate FKBP-CD28 fusion and was further subcloned into pEF6a. Bio-Pup(E) was generated with a bacteria derived carboxylase domain fused to the N terminus of PupE by overlapping PCR and subcloned into pEF6a. IL2-FKBP was subcloned into pCDNA3.1 between EcoR1 and HindIII sites. All constructs were verified by DNA sequencing.

Recombinant Protein Expression and Purification

His tagged protein purification. Plasmid encoding His-MATH was transformed into E. coli BL21(DE3). Cells were grown in 1 liter LB media supplemented with 100 μg/ml ampicillin at 37° C. until OD600 nm reached 0.8. Protein expression was induced with 0.2 mM IPTG and cells continue to grow at 18° C. over night. Cells were harvested by centrifugation, resuspended in lysis buffer (50 mM Tris pH 8.0, 200 mM NaCl, 1 mM DTT), and lysed by either sonication or French pressure cell press. The supernatant was isolated by centrifugation for 30 min at 4° C. at 24,000×g and purified by Ni-NTA affinity chromatography (GE Heathcare Life Sciences, cat. #17-5318-02) on a gravity column. Ni-NTA resin was washed with 20 column volumes (CV) of Lysis Buffer and then 10 CV of Wash Buffer (50 mM Tris pH 8.0, 200 mM NaCl, 20 mM Imidazole) before elution with Lysis Buffer (50 mM Tris pH 8.0, 200 mM NaCl, 250 mM imidazole). Glycerol was added to the purified protein to the final concentration of 5% and the protein samples were aliquoted and stored at −80° C.

GST Tagged Protein Purification.

Bacteria culture and induction protocol was similar to those for His tagged protein purification. Instead of using Ni-NTA resin, glutathione resin (GE healthcare life sciences, cat. #17-5132-02) was used for affinity purification and the elution buffer containing 10 mM reduced glutathione instead of 250 mM imidazole was used to elute protein from the resin. To remove the GST tag, precision protease was added at a weight ratio of 1:200 to cleave GST off target protein at 4° C. over night. Size exclusive gel filtration chromatography (SD200, GE healthcare life sciences) was used to separate GST and target protein in buffer containing 20 mM Tris pH 8.0, 150 mM NaCl, and 1 mM DTT.

In Vitro Pup Modification Assay

Pup modification were assayed at 37° C. for 30 min with purified recombinant proteins in a 20 µl reaction volume with 20 mM Tris 8.0, 100 mM NaCl, 10 mM ATP, and 15 mM $MgCl_2$. The reaction also contains purified 1 µM PUP-IT, 10 µM Pup(E) or 10 mM bio-DE28. All the reactions were stopped by direct addition of 6×SDS loading buffer and analyzed on 4-20% SDS-PAGE gels (Genescript, cat. #M42015C).

Peptide competition assay (as in FIG. 2d) was performed in the presence of different peptides. Free pep1 (sequence LACDEVTSTTSSSTA, SEQ ID NO: 12) and control peptide (sequence LACDEDTAAASSSTA, SEQ ID NO: 15) were synthesized and purified to >98% pure, confirmed by mass spectrometry. The peptides were dissolved in water and pH adjusted with Tris buffer to 7, stored as 2 mM stock in −80° C. The reactions were set up with 1 µM pup$^{SBC1}$, 0.2 µM His-MATH, and 8 µM Pup(E). Different amount of free pep1 or control peptide was added to each reaction to make the final peptide concentration at 1, 2, 4, 8, 16, 32, 64, 128, 256, and 512 µM. All the reactions were stopped by direct addition of 6×SDS loading buffer and analyzed on 4-20% SDS-PAGE gels, followed by immune-blotting with anti-His antibody to identify both unmodified and modified MATH. The density of modified MATH was quantified with ImageJ and then plotted with GraphPad Prism 6.

Stable Cell Line Generation

Jurkat (clone E6-1, ATCC TIB-152) T cells were maintained in a cell culture incubator at 37° C. with 5% $CO_2$. Cells were cultured in RPMI 1640 (Gibco, cat. #C22400500CP) supplemented with 10% fetal bovine serum (FBS) (Gibco, cat. #10099-141). To generate the iPUP Jurkat cell line, we subcloned Bio-Pup(E)-IRES-BFP into the expression vector of the Tet-On system. Each plasmid was packed into lenti-virus then co-transfected Jurkat cells. 48 hours after transfection, 2 µg/ml doxcyline was added to cell culture for another 24 hours. BFP positive cells were sorted into 96 well plates with 1 cell/well for single clone selection. Three weeks after, each clone was examined for BFP expression by flow cytometer with or without doxcyline induction. The expression of bio-Pup(E) in BFP positive cells were also confirmed by western blot.

Transient Transfection Based PUP-IT Application

Two plasmids (pEF6a backbone as described in the molecular cloning section), one contains bio-Pup(E), another contains PUP-IT fusion protein, were co-transfected to wild type Jurkat cells by electroporation. Basically, Wild type Jurkat cells were grown in medium without antibiotics, then harvested and suspended at 40 million/ml. 300 µl cells (12 million cells in total) were gently mixed with 30 µg plasmid DNA and then transferred to 0.4 cm cuvette (Bio-Rad, cat. #1652088). Pulse electroporation was performed at 1000 µF, 250 V (BioRad GenePulser). After the pulse, cells were kept in room temperature for 15 minutes, then transferred to pre-warmed recovering medium to grow. 24 hours after transfection, 4 µM biotin were added to cell medium. Cells were harvested after another 24 hours for either mass spectrometry sample preparation (see stable cell line based PUP-IT application for details of sample preparation) or western blot characterization.

Stable Cell Line Based PUP-IT Application

PUP-IT$^{CD28}$ and controls were introduced into iPUP Jurkat cell line through lenti-virus transduction. Plasmid coding PUP-IT$^{CD28}$ also contains GFP. GFP positive cells were sorted and amplified for further experiments.

PUP-IT transfected iPUP cells were grow to 3×10$^7$ cells at the concentration of 5×10$^5$ cells/ml. Biotin and doxycycline were added to medium at 4 µM and 2 µg/ml respectively. After 36 hours, cells were harvested, washed, and lyzed in 3 ml M-Per lysis buffer (Pierce, cat. #78501) supplemented with protease inhibitor (Pierce, cat. #B14001). Urea powder was added to cell lysate to make the final concentration at 8 M. The lysate was reduced with 10 mM DTT at 56° C. for 1 hour, aminocarbonyl modified at Cys by 25 mM iodoacetamide in dark for 45 minutes, then quenched by additional 25 mM DTT. The lysate was mixed with 50 µl streptavidin magnetic beads (Pierce, cat. #88816) and incubated on a rotator at room temperature for 1 hour. Beads were washed extensively with buffer 1 (50 mM Tris 8.0, 8 M Urea, 200 mM NaCl, 0.2% SDS), buffer 2 (50 mM Tris 8.0, 8 M Urea), buffer 3 (50 mM Tris 8.0, 0.5 mM EDTA, 1 mM DTT) sequentially, then with 100 mM ammonium carboxylate. 6 µg trypsin (Promega, cat. #V5280) was used for on-beads trypsin digestion over night at 37° C. The digested peptides were collected and cleaned with ZIPTIP (Millipore, cat. #ZTC18S096) before analysis with mass spectrometry.

Mass Spectrometry and Data Analysis

Peptides were separated and analyzed on an Easy-nLC 1000 system coupled to a Q Exactive HF (both—Thermo Scientific). About 2 µg of peptides were separated in an home-made column (75 µm×15 cm) packed with C18 AQ (5 µm, 300 Å, Michrom BioResources, Auburn, Calif., USA) at a flow rate of 300 nL/min. Mobile phase A (0.1% formic acid in 2% ACN) and mobile phase B (0.1% formic acid in 98% ACN) were used to establish a 60 min gradient comprised of 2 min of 5% B, 40 min of 5-30% B, 6 min of 30-45% B, 2 mM of 45-90% B and 10 min of 90% B. Peptides were then ionized by electrospray at 2.3 kV. A full MS spectrum (375-1400 m/z range) was acquired at a resolution of 120,000 at m/z 200 and a maximum ion accumulation time of 20 ms. Dynamic exclusion was set to 30 s. Resolution for HCD MS/MS spectra was set to 30,000 at m/z 200. The AGC setting of MS and MS$^2$ were set at 3E6 and 1E5, respectively. The 20 most intense ions above a 1.7E4 counts threshold were selected for fragmentation by HCD with a maximum ion accumulation time of 60 ms. Isolation width of 1.6 m/z units was used for $MS^2$. Single and unassigned charged ions were excluded from MS/MS. For HCD, normalized collision energy was set to 25%.

The raw data were processed and searched with MaxQuant 1.5.4.1 with MS tolerance of 4.5 ppm, and MS/MS tolerance of 20 ppm. The UniProt human protein database (release 2016_07, 70630 sequences), the sequence of A4QE80 and database for proteomics contaminants from MaxQuant were used for database searches. Reversed database searches were used to evaluate false discovery rate (FDR) of peptide and protein identifications. Two missed cleavage sites of trypsin were allowed. Oxidation (M), Acetyl (Protein N-term), deamidation (NQ) and GGE (K) were set as variable modifications. The FDR of both peptide identification and protein identification is set to be 1%. The option of "Second peptides", "Match between runs" and "Dependent peptides" was enabled. Label-free quantification was used to quantify the difference of protein abundances between different samples.

Cell Surface Pup Modification Assay

Jurkat cells were transiently transfected with FKBP-CD28-IRES-mCherry then sorted for mCherry positive cells. Raji cells were transfected with GFP and sorted. $1 \times 10^5$ GFP positive Raji cells were mixed with $2 \times 10^4$ mCherry positive Jurkat in the presence of 1 µM FRB-PafA, 1 µM rapamycin, 2 µM bio-DE28, 4 ng/ul SEE peptide, 10 mM ATP and 15 mM $MgCl_2$ in cell culture medium. The mixed cells were incubated in cell culture incubator at 37° C. for 30 minutes, washed with cold PBS twice, then incubated with streptavidin-Cy5 (Jackson, cat. #016-170-084, dilution factor 1:300) on ice for 30 minutes, washed again and resuspended in PBS for confocal microscope observation and flow cytometry analysis.

$1 \times 10^5$ Jurkat cells were first activated by plate coated anti-CD3 and anti-CD28 antibodies as previously described. Cell surface PUP-IT reactions were assayed in 150 µl volume in the presence of 0.5 µM IL2-FKBP, 1 µM FRB-PafA, 2 µM rapamycin, 2 µM bio-DE28 as well as ATP and $MgCl_2$. Cells were incubated at 37° C. for 30 minutes then stained with streptavidin-APC (Jackson, cat. #016-600-084, dilution factor, 1:500), anti-CD69-PE (Biolegend, cat. #310910, dilution factor, 1:500), or anti-CD25-PE (Biolegend, cat. #302606, dilution factor, 1:500) for flow cytometry analysis.

Quantification and Statistical Analysis

Quantitative data are presented as means±standard error of the mean (SEM). The SEM was calculated using Prism Graphpad and error bars represent one SEM from the mean. The statistical significance was assessed using p values calculated using the unpaired Student's t test (two-tailed) in either Prism or Perseus. The number of experiments (n) used for the statistical evaluation was specified in the figure legend.

Results

Biochemical Characterization of the PUP-IT System

Figure 1B:
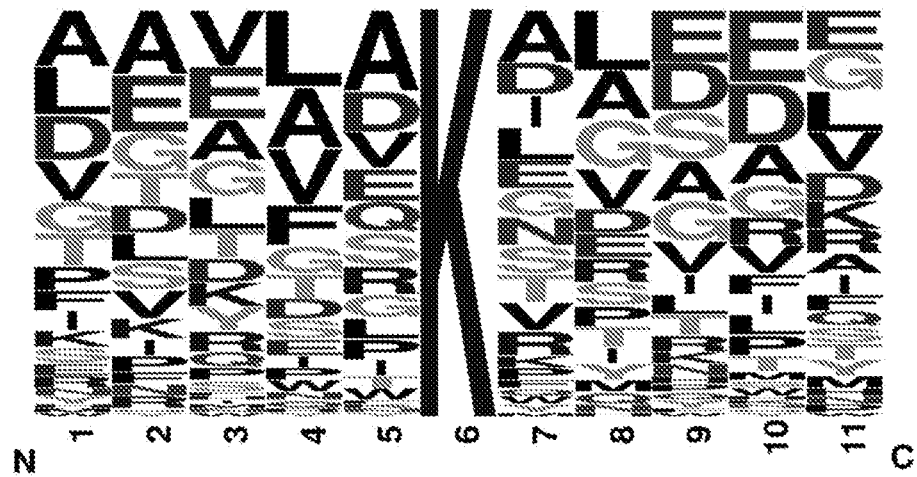
Figure 1C:
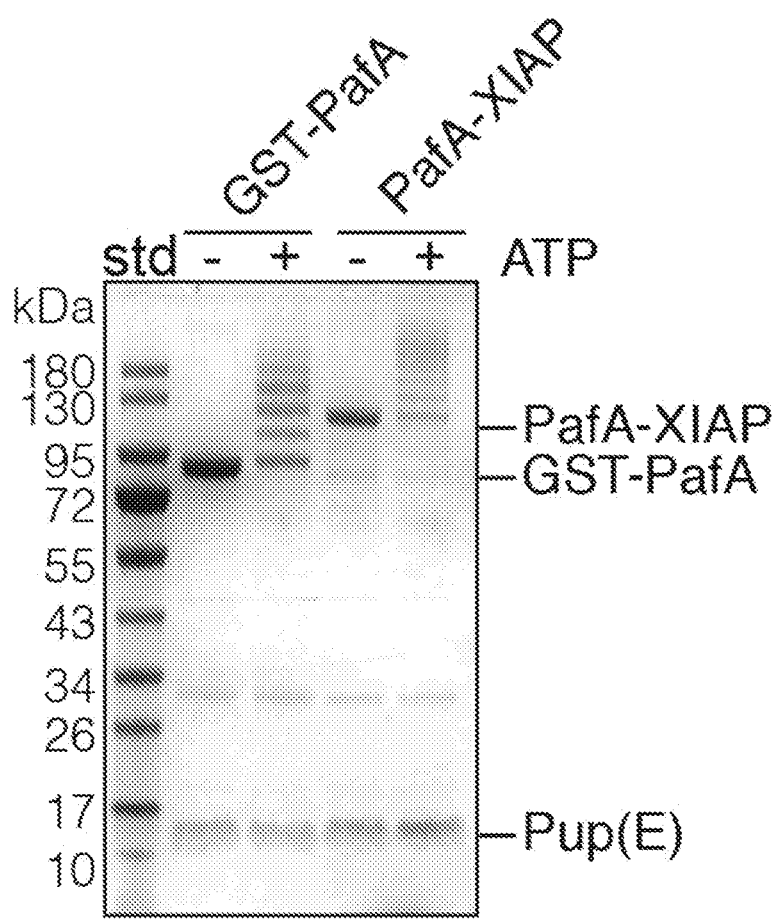
Figure 1D:
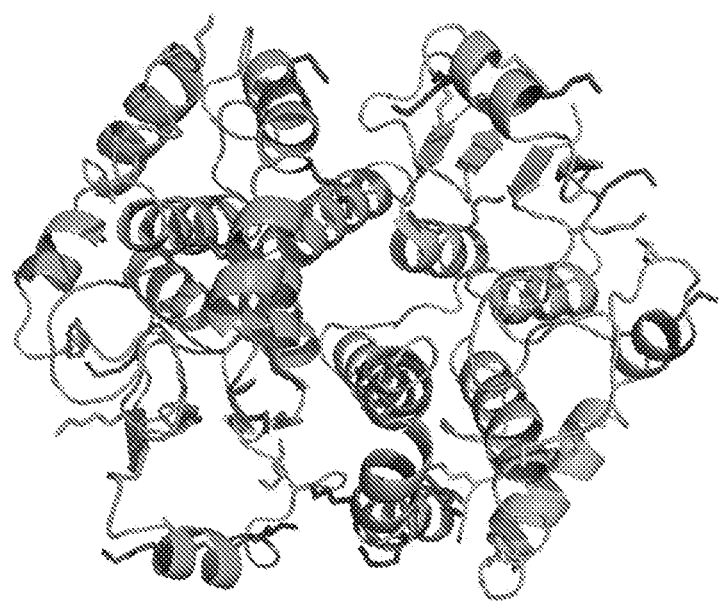

PafA is a Pup ligase that targets substrate lysine. Based on the results of previous mass spectrometry data, we decided to align all Pup modified sequences to see if any consensus sequences existed. Our results showed no obvious consensus sequence for the Pup modification site except the critical lysine residue (FIG. 1b). To further test if PafA is promiscuous at the residues around the target (lysine), we fused PafA with a non-substrate protein, either GST (26 kDa) at the N terminus or XIAP (55 kDa) at the C terminus. With purified proteins, the fusion of relatively large protein domains at either terminus of PafA does not interfere with PafA enzymatic activity. In addition, we observed tremendous protein ladders, indicating GST-PafA and PafA-XIAP are self-modifying (FIG. 1c). To identify the modification sites, we cut the modified protein bands for mass spectrometry characterization. Our results identified 10 lysine residues on the GST surface, labeled with an extra 243 Dalton mass, indicating GGE modifications on lysine side chain (FIG. 1d). All these lysines have different primary sequence context and are evenly distributed on the GST surface, further indicating that the ligation of Pup(E) to substrate lysine is independent of the primary sequence and that Pup labeling is promiscuous towards the attached protein.

Figure 1E:
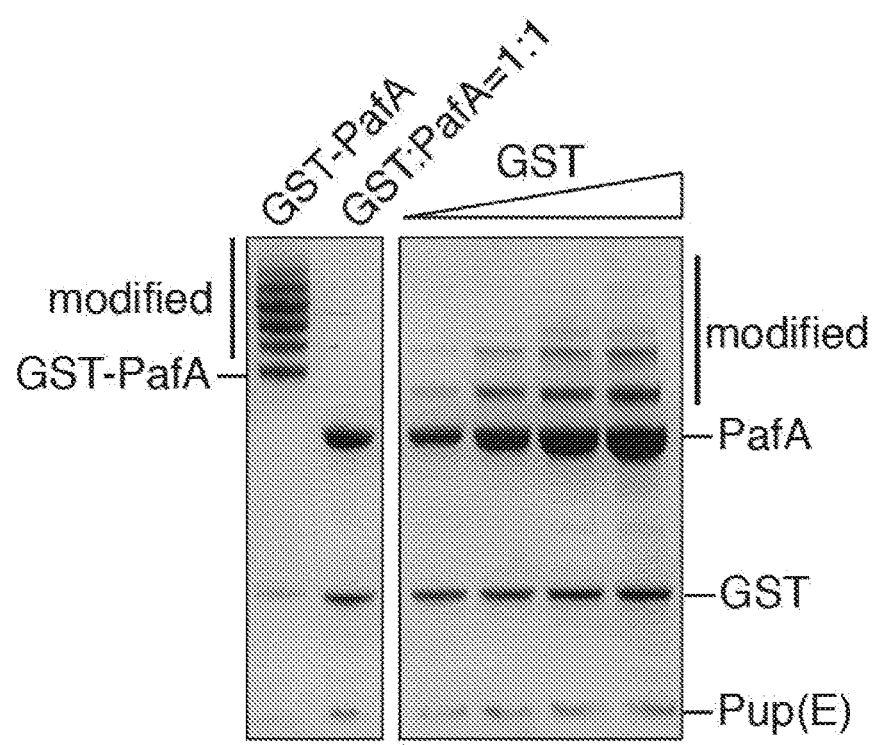

We further addressed whether PafA-mediated protein labeling is based on proximity. We mixed PafA with GST at 1:1 but did not observe any GST modification (FIG. 1e). Even gradually increasing PafA concentration as high as possible still did not yield any GST modification (FIG. 1e). It has been shown that BioID can non-specifically label unrelated protein in solution. We observed some self-modification of PafA at very high concentration but barely any GST modification. These results are consistent with the molecular mechanism of PafA activation and ligation, suggesting PafA might be a better ligase with promiscuous substrate recognition but higher specificity since the activated intermediate Pup(E) cannot freely diffuse from the enzyme.

Figure 1F:
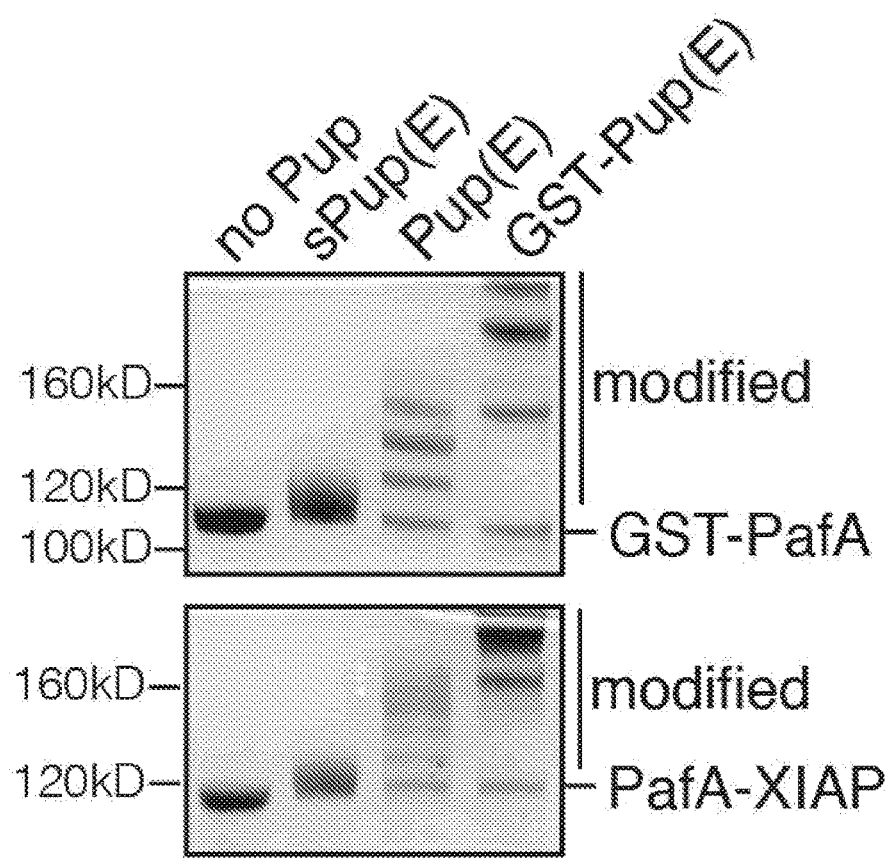

To extend PUP-IT application, we tested different forms of Pup as the substrate for PafA. The N terminus of Pup(E) can be modified with various tags without loss of function. The 64 amino acid Pup can also be truncated to a shorter peptide, minimally 28 amino acids, but retain its conjugation ability to target lysine residues (FIG. 1f). We also fused a bacteria-derived carboxylase domain to Pup(E), modifying the cells to contain biotin. We use this carboxylase fused Pup(E) (bio-PupE) protein and bio-DE28 (biotin-DSLL-DEIDGLLENNAEEFVRSYVQKGGE, SEQ ID NO: 2) peptide for the remaining study.

PUP-IT Can Label Weak Protein-Protein Interactions

Figure 2A:
FIG. 2a-d demonstrate that PUP-IT labels weak protein-protein interactions. (a) The model system used to study weak interactions. MATH domain from human protein SPOP interacts with different peptides with different affinity, ranging from 3.7 µM to 266 µM. PUP-IT$^{pep}$ represents PafA fused to different peptides. The sequences of each peptide are LACDEVTSTTSSSTA (pep1, SEQ ID NO: 12), TLFPDVSSSTHPYHG (pep2, SEQ ID NO: 13), and SELD-SPSSTSSSSGI (pep3, SEQ ID NO: 14). (b) With purified GST-MATH protein or His-MATH protein, different PafA-pep can modify MATH protein even with the weakest binder (pep3) in an ATP dependent manner. The modified MATH is shown as higher molecular weight bands in a coomassie stained gel. (c) MATH is modified in cells. Myc tagged MATH and V5 tagged PUP-IT$^{pep}$ were co-transfected in cells with bio-Pup(E). Immunoblots show the modification of MATH domain in cells. (d) Pup modification of MATH is specific and depends on the direct interaction between peptide and MATH domain. Free pep1 peptide or a mutated pep1 peptide (LACDEDTAAASSSTA, SEQ ID NO: 15, known to have defect on MATH binding, as a control peptide) is added to the in vitro assay to competitively inhibit MATH modification. The left panel is a representative gel image and the right panel is the inhibition curve with three experimental repeats. Error bars represent SEM.
Figure 2B:
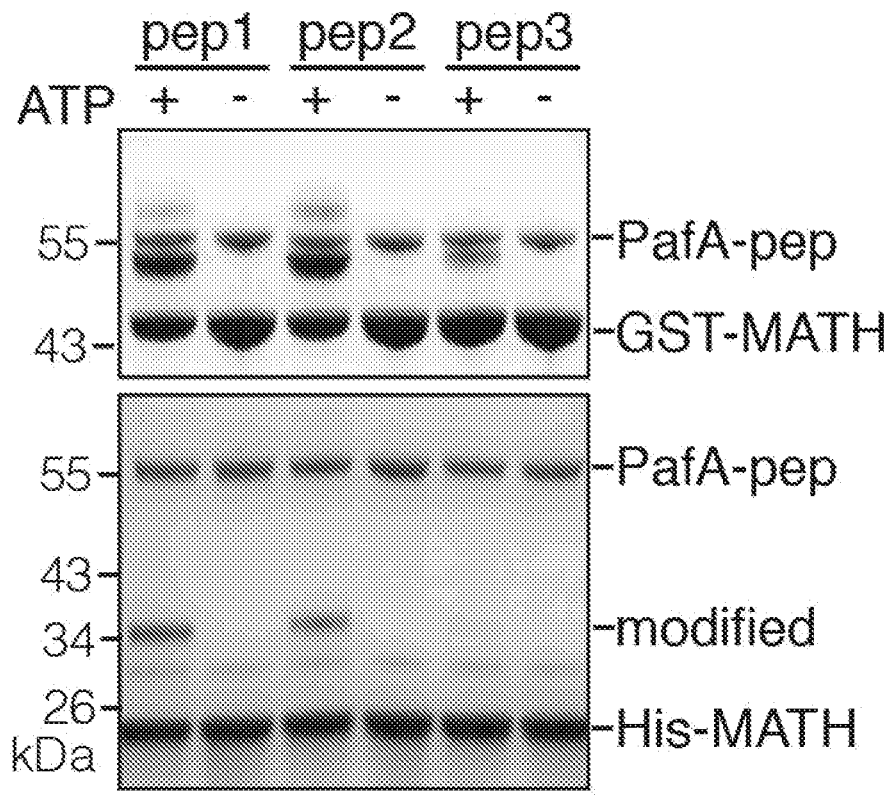

Next, we address whether PUP-IT can label weak and transient interactions which are hard to detect with traditional methods. We choose a model system where the SPOP MATH domain binds to various peptides with different affinity. SPOP is a subunit of Cul3 ubiquitin ligase that specifically recognizes different substrates. The interaction between SPOP and substrates is mediated through the MATH domain on SPOP and a short peptide on substrates. It's known that the MATH domain from human SPOP interacts with pep1, pep2 and pep3, all derived from SPOP substrates, with a dissociation constant (Kd) of 3.7 µM, 76 µM and >250 µM respectively (FIG. 2a). A Kd value in micro-molar range typically indicates a weak protein-protein interaction and it is usually difficult to pull down by traditional affinity purification. We designed PUP-IT$^{pep}$ from PafA fused to the three different peptides and examined PUP-IT$^{pep}$'s ability to modify the MATH domain. With either GST-tagged or His-tagged MATH as the substrate, we observed higher molecular weight modifications with all three PUP-IT$^{pep}$ even for the weakest binder pep3 (FIG. 2b). In addition, the modification extent of MATH seems to be correlated with the affinity between MATH and the corresponding peptide.

Figure 2C:
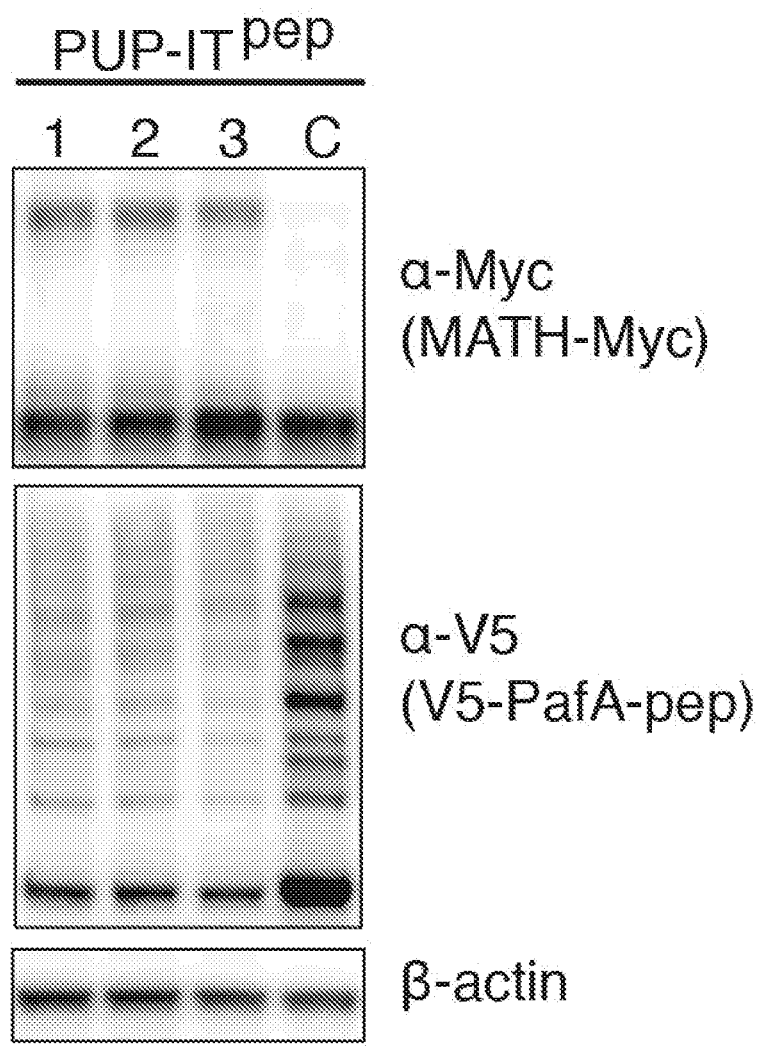

To test if PUP-IT can still label weak interactions up to 200 µM Kd within cells, we co-transfected cells with PUP-IT$^{pep}$ and MATH. Consistent with in vitro study, we observed modification of MATH protein in cells, indicating the PUP-IT system is suitable for cellular study (FIG. 2c). Both in vitro and cellular experiments demonstrate PUP-IT can actively label prey protein with Pup(E) in the context of weak protein-protein interactions.

Figure 2D:
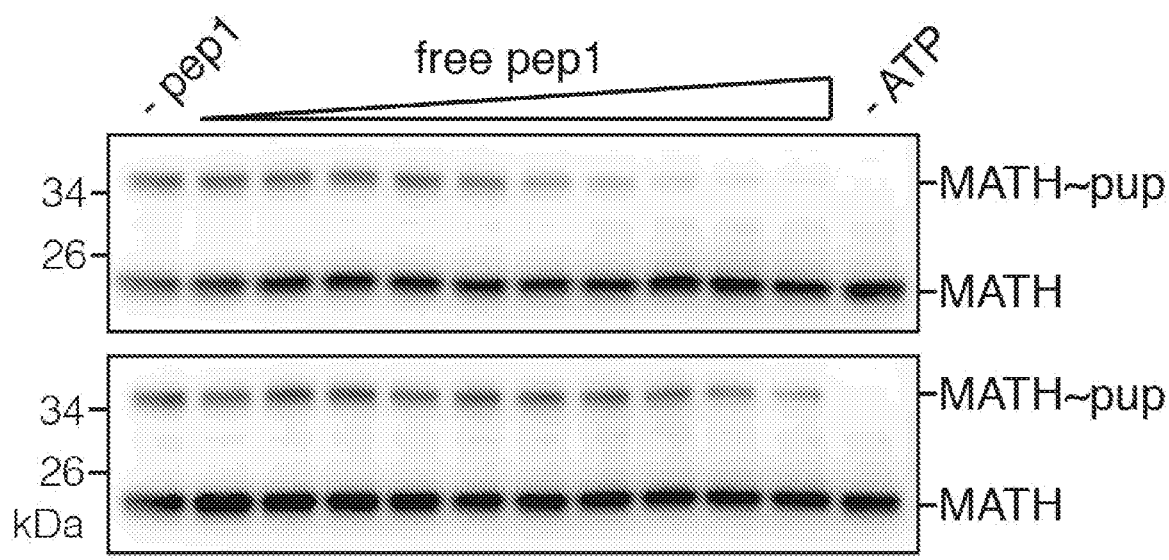

Despite the weak interaction between MATH and different peptides, Pup modification on MATH is still specifically dependent on the direct interaction between MATH and the peptide. We synthesized a wild type pep1 peptide as well as a pep1 mutant (control) that has a defect MATH binding. In the reaction of PUP-IT$^{pep1}$, we added free pep1 and observed a dose-dependent inhibition of MATH modification (FIG. 2d). However, the reaction could not be fully inhibited by the control peptide pep1(mut), suggesting that the specific interaction between MATH and pep1 is required for Pup(E) labeling.

Application of PUP-IT to Identify the Interactome of CD28 Cytosolic Tail

Given the sensitivity of our PUP-IT system towards identifying weak protein-protein interactions and the stability of covalent bonds formed between Pup(E) and target proteins, it is potentially ideal for membrane protein interactome study. Typically, membrane proteins are receptors that form weak and transient bonds with cytosolic signaling proteins to initiate cell signaling. In addition, membrane proteins may associate with other membrane proteins through the trans-membrane domain, an area difficult to observe with traditional methods.

Figure 3A:
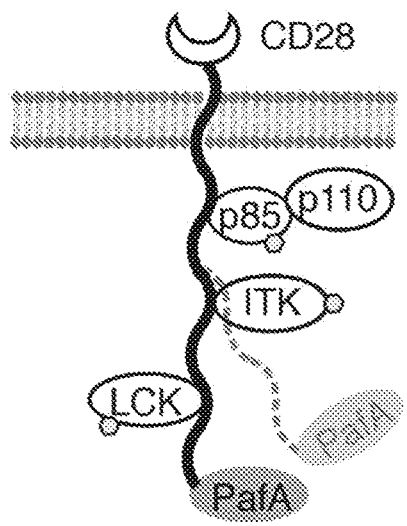
FIG. 3a-d show that PUP-IT can be used to identify cytosolic binding proteins of membrane receptor. (a) Schematic view of PUP-IT$^{CD28}$. LCK, ITK, p85 are proteins known to interact with the C terminal tail of CD28. (b) PUP-IT$^{CD28}$ mediates p85 modification of Pup. Different PUP-IT$^{CD28}$ variants and bio-Pup(E) were co-transfected in Jurkat cells. Western blot show additional bands above p85 blot. The higher molecular weight band is further approved to be bio-Pup(E) modification with streptavidin pull down of bio-Pup(E) under denaturing condition then blotted with anti-p85 antibody. (c) Identification of CD28 interacting proteins by mass spectrometry. The spectral counts are combined from duplicate runs and plotted with each dot represents a protein identified. PUP-IT$^{CD28}$ and PUP-IT$^{tailless}$ datasets are compared. The red dots are examples of known CD28 interacting proteins. (d) Identification of CD28 interacting proteins by comparing the spectral counts from PUP-IT$^{CD28}$ and PUP-IT$^{5AA}$ datasets.

We first applied the PUP-IT to membrane receptor CD28. CD28 is a co-stimulating receptor normally expressed on the surface of T cells. Engagement of CD28 by its ligands B7s (CD80 and CD86) provides a second signal to synergize with TCR (T cell receptor) signaling to induce naive T cell activation. Blocking CD28-mediated co-stimulation has been shown to be clinically important. It is therefore important to understand the interactome of CD28. Previous studies have identified p85, LCK, and ITK as downstream molecules that directly interact with the cytosolic tail of CD28 (FIG. 3a). In order to validate the application of PUP-IT on membrane protein, we made PUP-IT$^{CD28}$ by fusing PafA to the C terminal tail of full length CD28. For controls, we also made PUP-IT containing a tail-less CD28 (residues 1-179), a short tail CD28 (5AA, residues 1-184), a p85 binding deficient mutant (Y191F) and an LCK binding deficient mutant (Y209A). We observed a high molecular weight band in the PUP-IT$^{CD28}$ transfected sample, suggesting Pup(E) modification of p85. By contrast, the tailless, the short tail and Y191F PUP-IT$^{CD28}$, all lacking a p85-binding site, could not modify p85. Y209A PUP-IT$^{CD28}$ functioned similarly to the wild type (FIG. 3b).

Figure 3B:
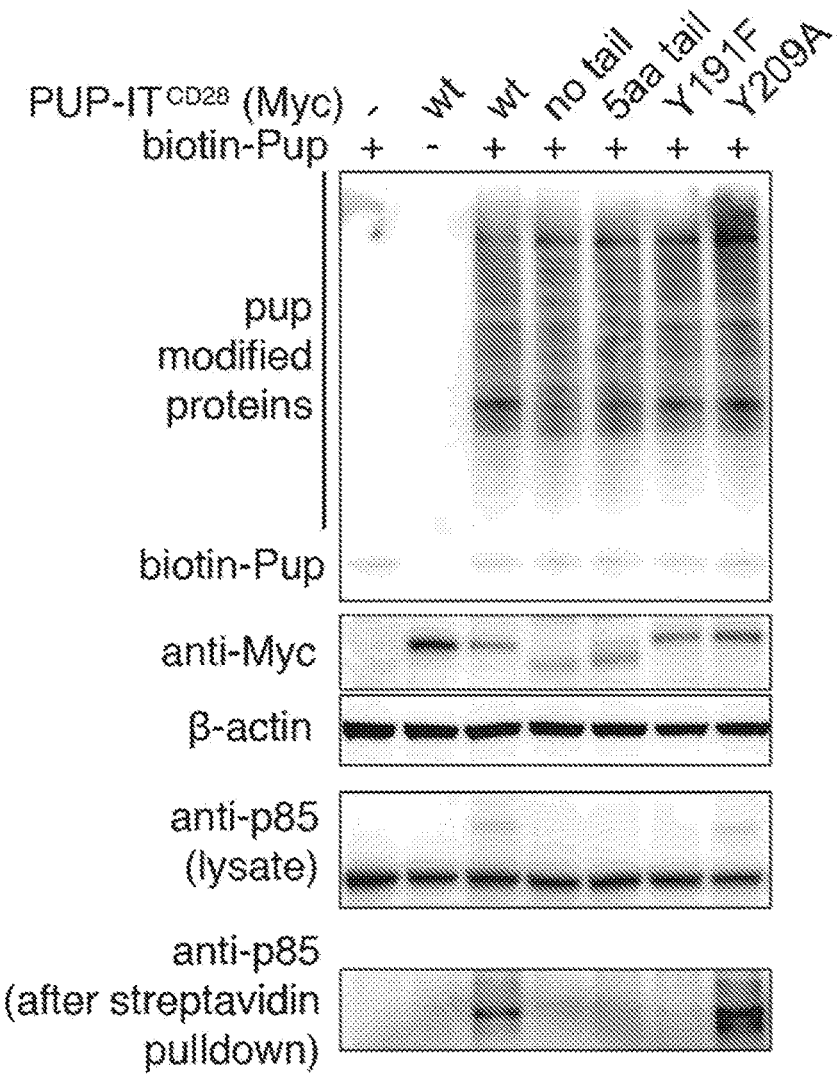
Figure 3C:
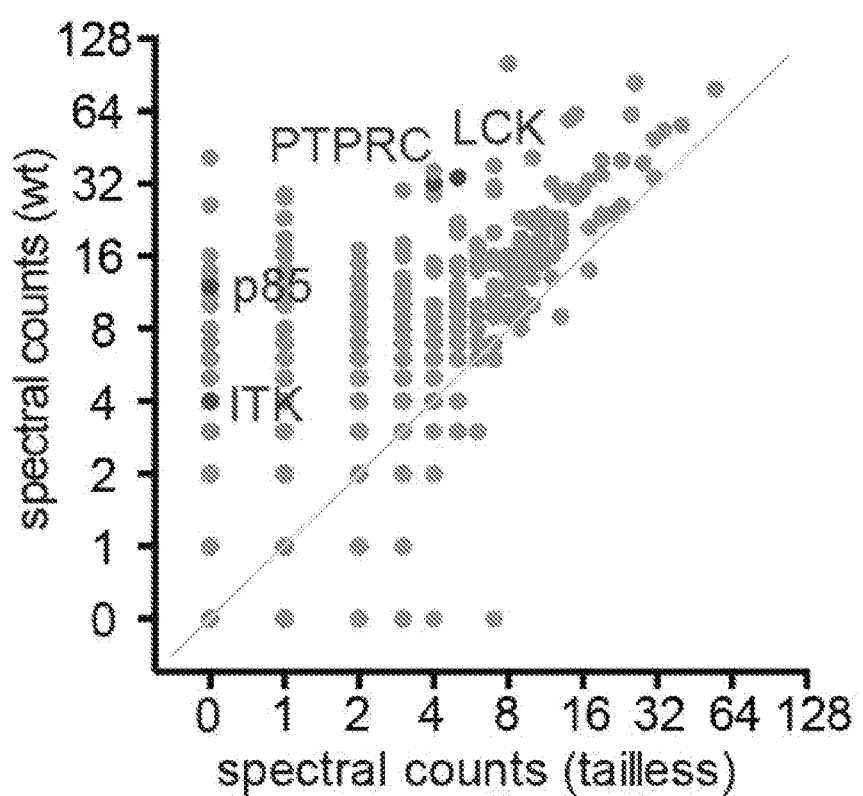
Figure 3D:
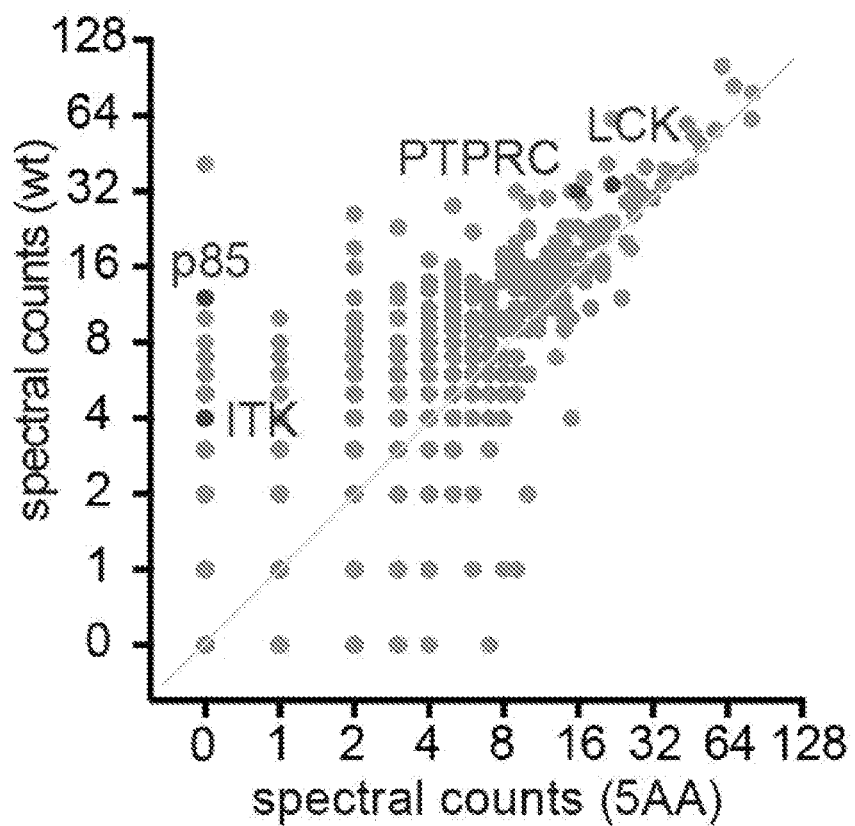

To our surprise, in the presence of PUP-IT$^{CD28}$ and bio-Pup(E), there was a significant amount of modification in the cellular proteins, showing a smearing of biotin signals in the immuno-blot experiment (FIG. 3b). To identify all Pup(E)-modified proteins and their new CD28 binding partners, we co-transfected Jurkat cells with PUP-IT$^{CD28}$ together with biotin-tagged Pup, followed with streptavidin pulled down under denatured conditions, then we initiated LC-MS/MS characterization of Pup-modified proteins. For each experiment, we included biological duplicates. In total, we identified 712 proteins with full length CD28, 591 with tailless CD28, and 645 proteins with short tail CD28 (5AA) (≥2 peptides for each protein). We sorted the data based on spectral counts to highlight the difference between wild type CD28 and the controls (FIG. 3c-d).

The identified proteins can be categorized into three groups. One group is shown by dots along the diagonal line with similar spectral counts in both PUP-IT$^{CD28}$ and PUP-IT$^{CD28\ tailless}$ experiments (FIG. 3c). These proteins are probably backgrounds. Some of the proteins in this group are endogenously-biotinylated proteins, such as carboxylase in mitochondria. The second group displays very different spectral counts in experiment duplicates, probably due to low protein coverage or overlapping MS signals. Most of the proteins in this group have only 2-3 peptides identified. Of greatest interest is the third group, categorized by significantly higher spectral counts in PUP-IT$^{CD28}$ samples but not in PUP-IT$^{CD28\ tailless}$ samples, indicating these proteins are highly enriched potential CD28 cytosolic tail-binding proteins. As expected, known CD28 tail-interacting proteins, such as p85, ITK, PTPRC and LCK, all fall into this group (FIG. 3c). Similar results were observed when comparing PUP-IT$^{CD28}$ and PUP-IT$^{CD28\ 5AA}$ (FIG. 3d).

In total, combining proteins identified in all experiments, we identified 202 proteins as potential CD28 tail-binding partners. With gene ontology analysis, we found some of the CD28 binding partners to be known molecules involved in T cell signaling. More interesting, there is another group of proteins highly enriched in our samples, mostly involved in protein translocation and membrane targeting. These proteins may be involved in CD28 synthesis and trafficking. We speculate PUP-IT$^{CD28}$ is actively ligating Pup(E) as soon as it is translated but before it is correctly transported to the cell surface.

PUP-IT Identifies Known CD28 Signaling Components as Well as Candidate Interacting Partners In addition to using its C-terminal tail, CD28 may also interact with proteins through the trans-membrane domain or the extracellular domain while it is still in the sorting process to the cell surface. In previous experiments, the controls we used were tailless CD28, with expectations of identifying those proteins that interact with the cytosolic tail of CD28. We compared CD28 to another unrelated membrane protein RNF13 to further identify all potential CD28 interacting proteins in a full spectrum.

Figure 4A:
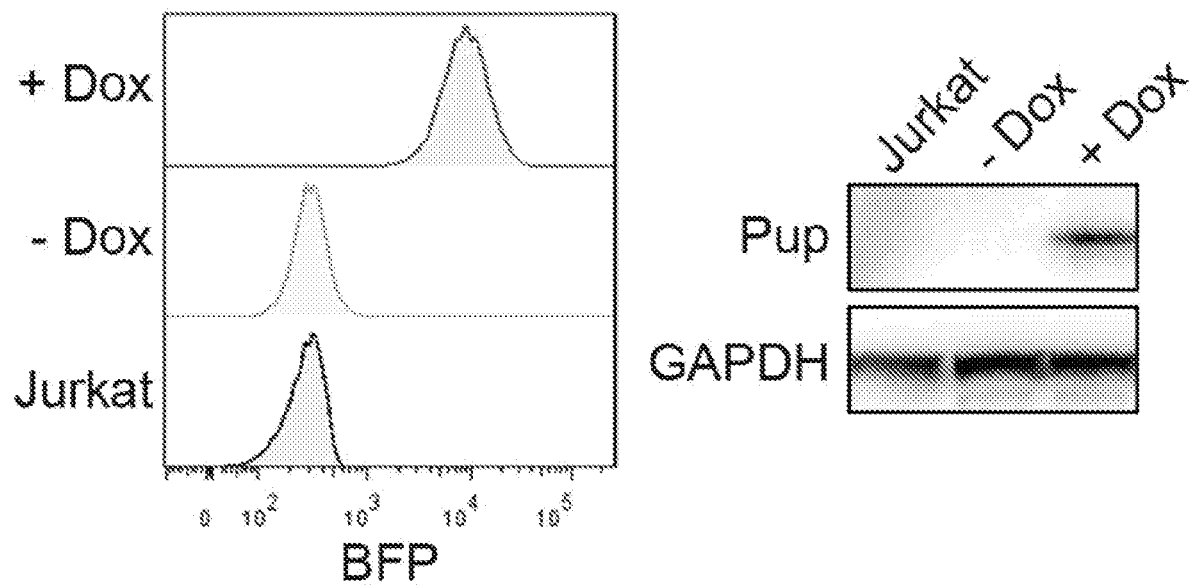
FIG. 4a-e present analysis of CD28 interacting protein which reveals four major groups of CD28 binding partners. (a) Generation of an inducible cell line (single cell clone) that conditionally expresses Pup. Pup was cloned under TET-ON promoter together with BFP (blue fluorescent protein) with IRES between two genes. Left, FACS analysis show the BFP expression was induced with doxycycline (Dox). Right, western blot show the expression of Pup is induced with Dox. (b) The Pearson correlation coefficient between the replicate mass spectrometry results of PUP-IT$^{CD28}$ and PUP-IT$^{RNF13}$ (control, an unrelated cell membrane protein). (c) Volcano plots of PUP-IT$^{CD28}$ interacting protein. Data points are plotted on the basis of LFQ-intensity from triplicate mass spectrometry experiments. The known CD28 interacting proteins were heighted in red. Green dots represent CD28 specific interacting proteins while blue dots represent RNF13 specific interacting proteins. (d) Gene ontology analysis of CD28 interaction proteins. The gene ontology software STRING (functional protein association networks) was used to analyze protein interactions. The thickness of the lines indicates the strength of data support. GGE modified peptides are identified from red-labeled proteins. PIK3R1 is the gene name of p85. (d) GGE modification sites are mapped on CDC42, RhoA and ARHGDIB crystal structures (PDB IDs 5C2J, 5FR2 and 1DS6). The modified lysines are highlighted in purple.
Figure 4B:
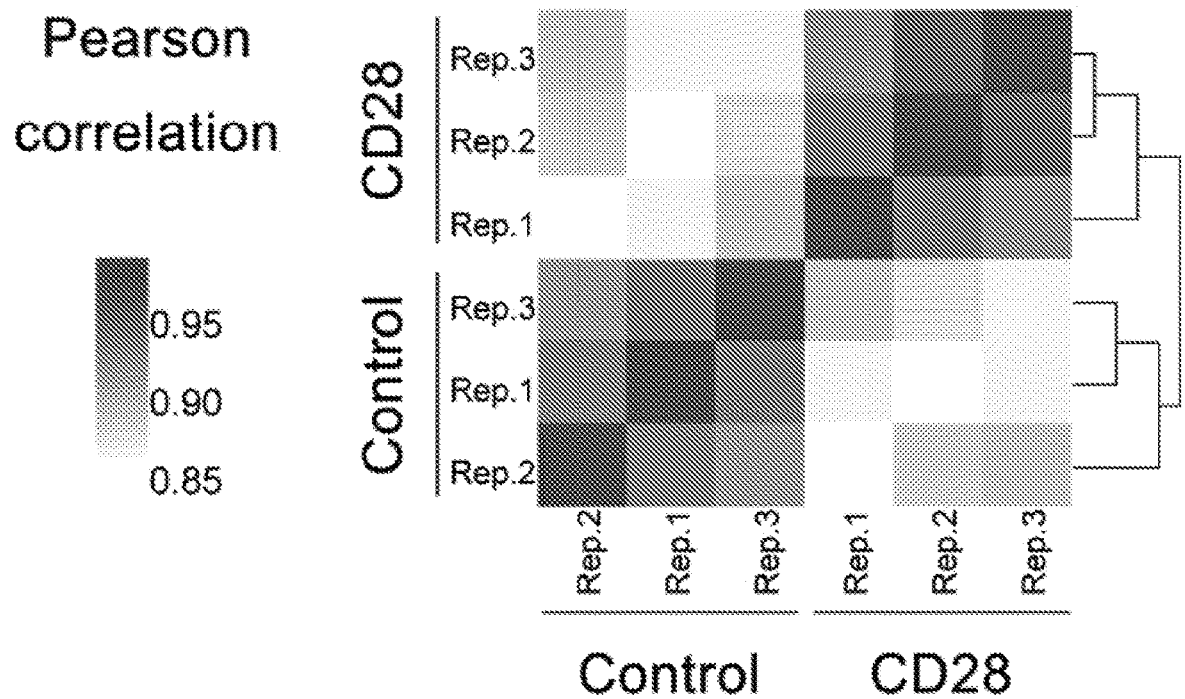
Figure 4C:
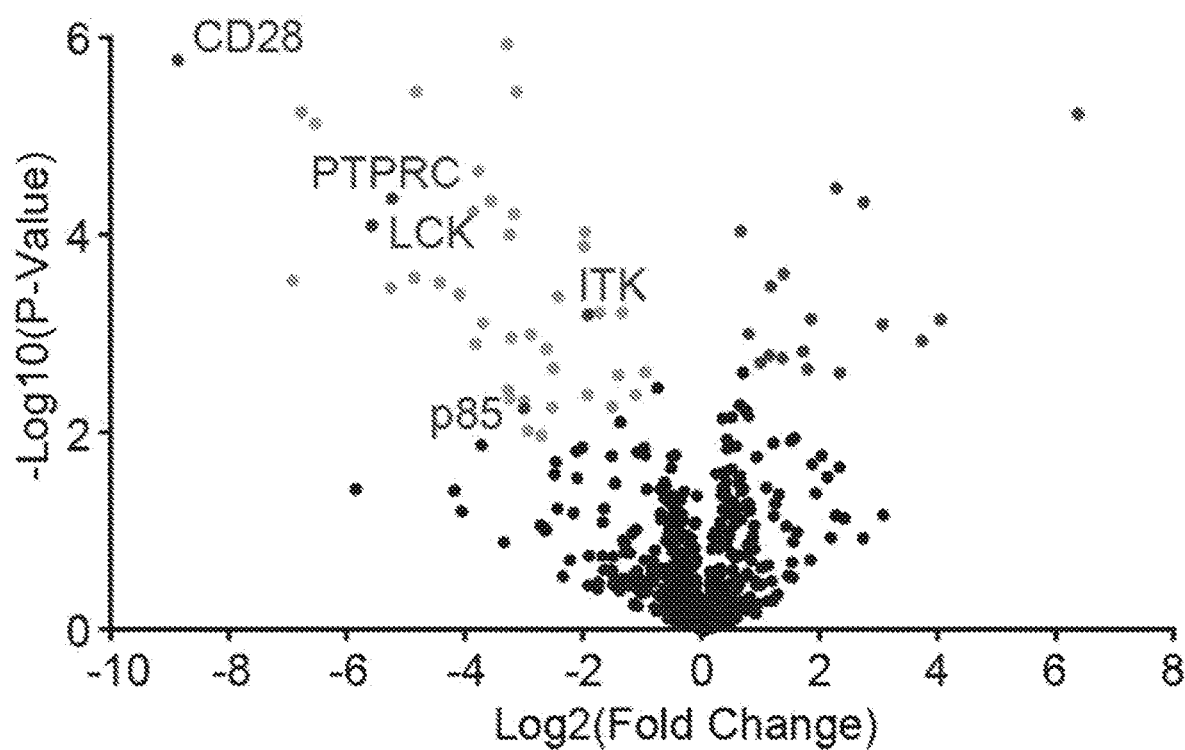
Figure 4D:
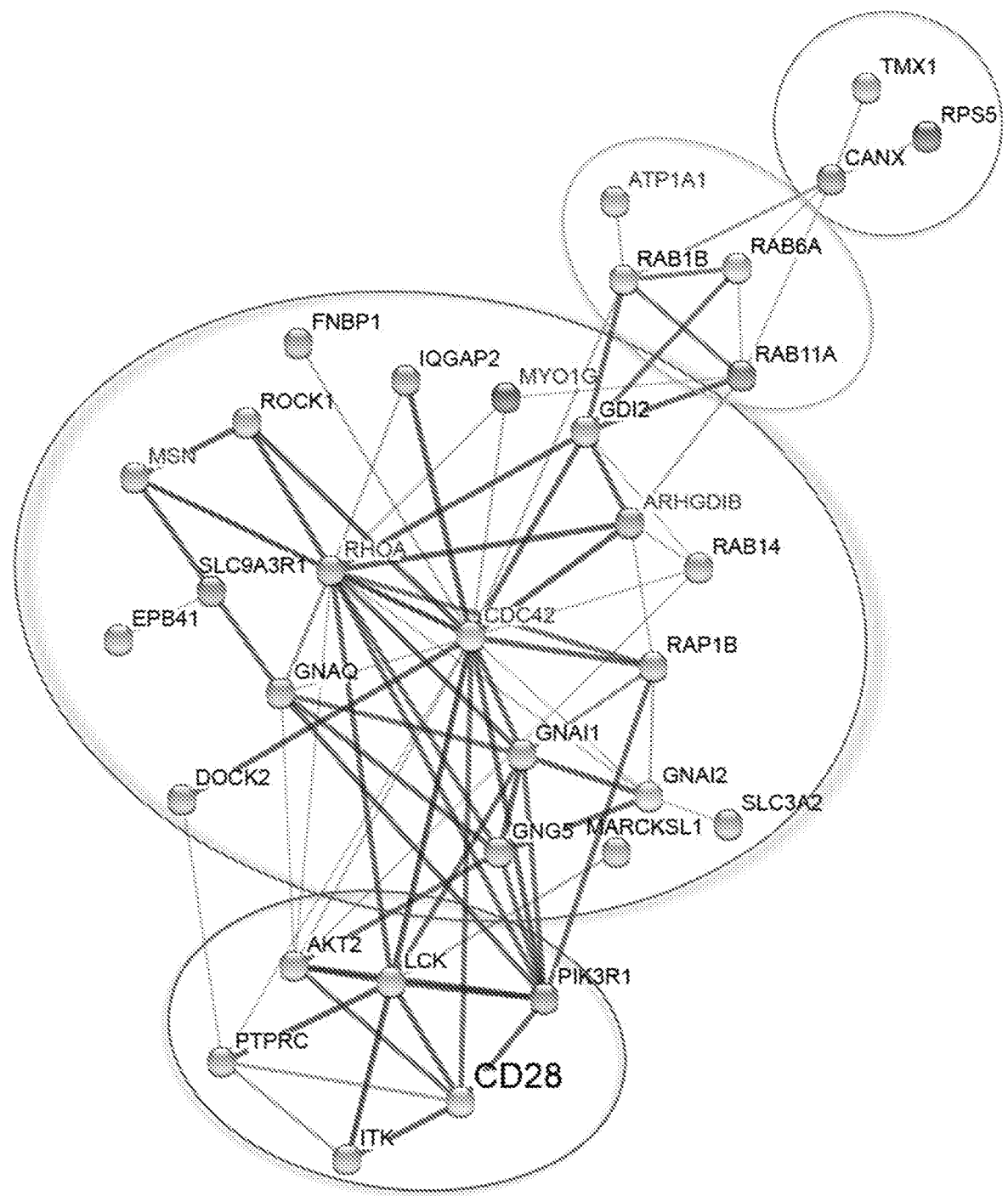

To further optimize PUP-IT labeling, we made a stable Jurkat cell line with Pup(E) expression controlled by the TET-ON system (FIG. 4a). After infecting the cells with PUP-IT$^{CD28}$, we waited for the protein to e expressed on the cell surface, then added doxycycline to induce Pup(E) expression, initiating the labeling process. The precise control of Pup(E) expression significantly reduced background and increased reproducibility (FIG. 4b). In triplicate experiments, we found 41 proteins that were uniquely identified in CD28 datasets with high confidence, including known CD28-interacting proteins, such as LCK, ITK, and p85 (FIG. 4c). All of the identified proteins were found to be well-associated by gene ontology analysis. 33 out of the 41 identified proteins could be mapped on a single connected STRING notes map, all well-connected to CD28 signaling (FIG. 4d). The interacting proteins were rougly divided into 4 groups, including CD28 signaling (red oval), cytoskeletal remodeling (green oval), protein folding and procession (purple circle), as well as vehicle transporting (cyan circle) (FIG. 4d). The latter two groups are all related to protein localization. These identified proteins may be important regulators for correct cell surface localization and trafficking of CD28.

Figure 4E:
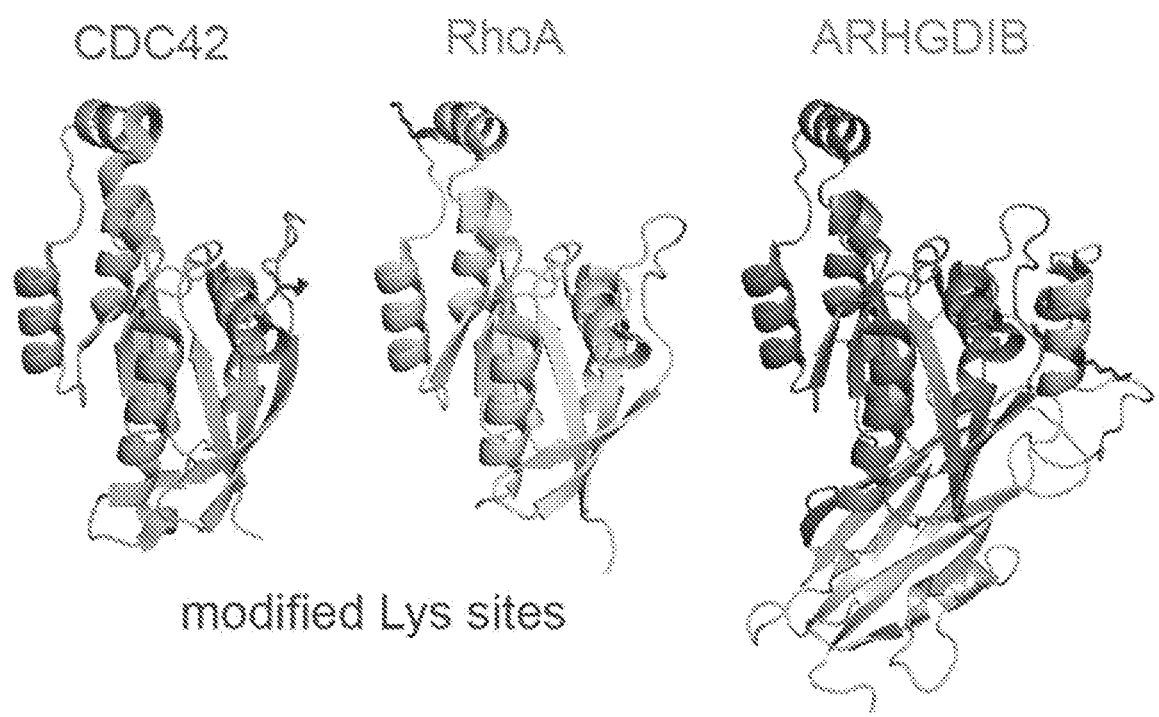

Notably, our dataset shows a large portion of CD28 interacting proteins is made up of GTPases or GTPase regulator. For some of these proteins, we detected GGE modification at specific lysine residues, strongly supporting the interaction between CD28 and those proteins (FIG. 4d). When mapped on available structures, those modified lysine sites are all located on protein surfaces, consistent with what we have observed with Pup modification of purified GST (FIG. 4e, FIG. 1d).

An Inducible PUP-IT System to Label CD28 Ligand Containing Cells

Figure 5A:
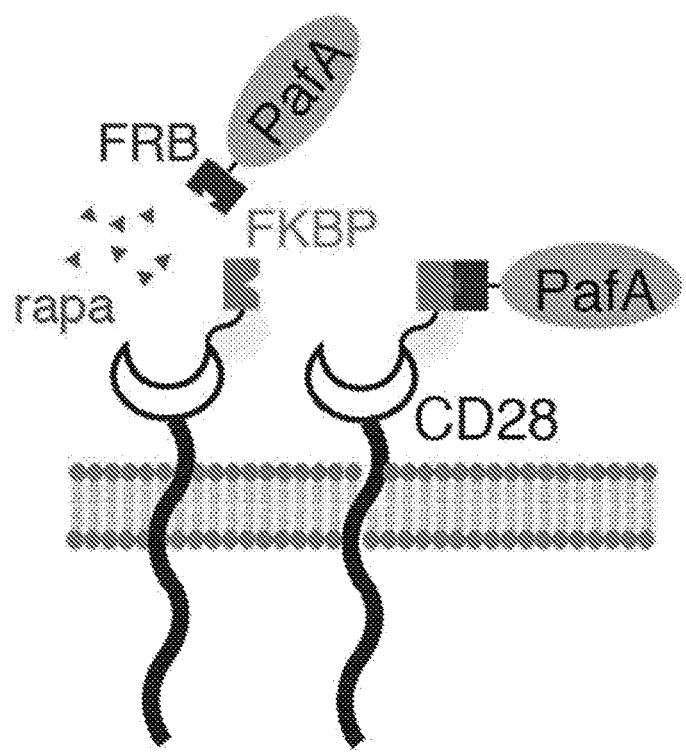
FIG. 5a-e show that PUP-IT can be used to label cell surface proteins. (a) Assembly of PUP-IT on cell surface. PafA is fused to FRB while FKBP is fused between the N terminal signaling peptide and CD28. In the presence of rapamycin, PUP-IT will be brought to the cell surface and forms a complex with CD28. (b) Cell surface can be labeled with the assembled PUP-IT. Jurkat cells are transfected with FKBP-CD28 and GFP. Cell surface Pup modification assay are performed with bio-DE28 with or without rapamycin. Cells are then stained with streptavidin-Alexa 647 to indicate biotin modification on surface. (c) Schematic view of PUP-IT$^{CD28-extracellular}$ mediated Raji cell labeling. (d) Assembled PUP-IT$^{CD28-extracellular}$ can label interacting Raji cells. Top panel, Jurkat (red) and Raji (green) surface labeling of bio-DE28 (blue) is dependent on ATP and rapamycin. Bottom panel, zoom-in view of the labeling sites on Raji. (e) PUP-IT$^{CD28\text{-}extracellular}$ mediated Raji cells labeling is not dependent on SEE. Similar experiments were set up as in d) but the fluorescence is detected with flow cytometer. The percentage of biotin positive cells is shown in the gated window.
Figure 5B:
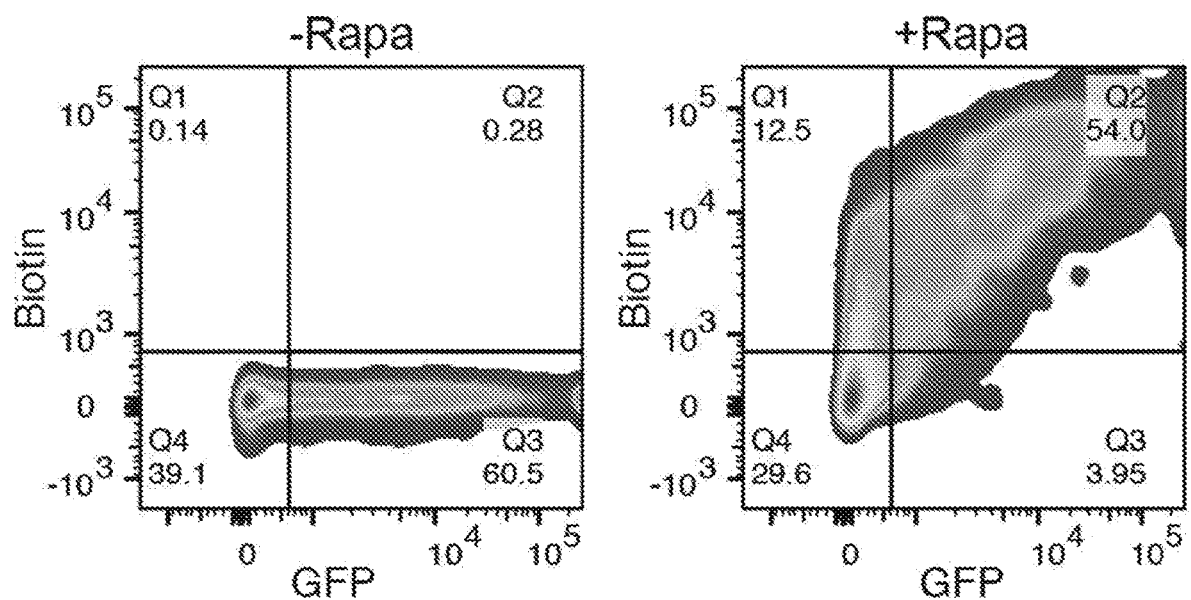

We next sought to test the possibility of applying PUP-IT in the extracellular context. CD28 cytosolic signaling is trigged by the extracellular binding of a CD28 ligand, such as CD86 and CD80 expressed on the surface of antigen-presenting cells. It would be useful if we could use PUP-IT to investigate the identity of cells that provide co-stimulatory signal to CD28-containing T cells. We tried to fuse PafA with the N terminus of CD28 to promote protein display on the cell surface but failed to reach observable expression, most likely due to protein-folding problems. Instead, we inserted a FKBP sequence between the CD28 signaling peptide (residues 1-19) and the rest of CD28 to express FKBP-fused CD28 (FIG. 5a). Rapamycin, a small molecule compound, can induce heterodimerization of protein FKBP and FRB. In the presence of recombinant purified FRB-PafA, rapamycin and bio-DE28 peptide, our Jurkat cell surface (likely CD28 itself) was labeled with a biotin signal, which indicates that PUP-IT labeling is active outside of the cells. (FIG. 5b).

Figure 5C:
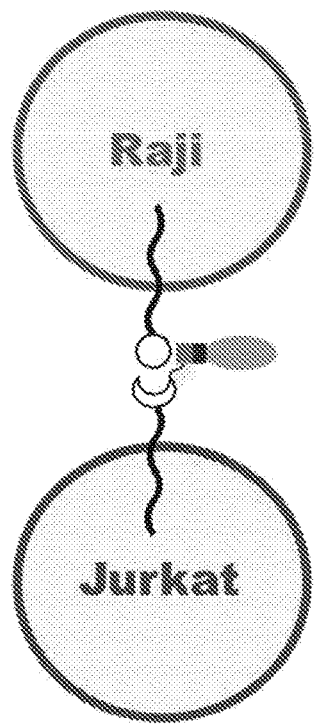
Figure 5D:
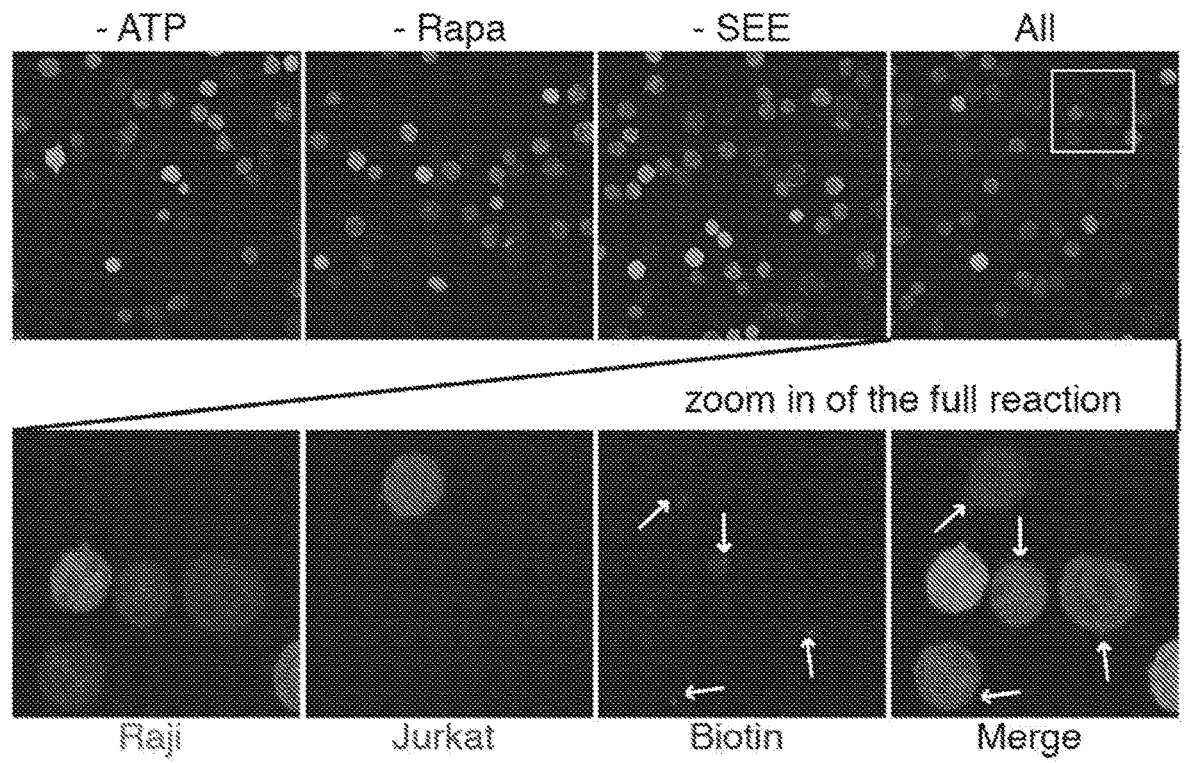
Figure 5E:
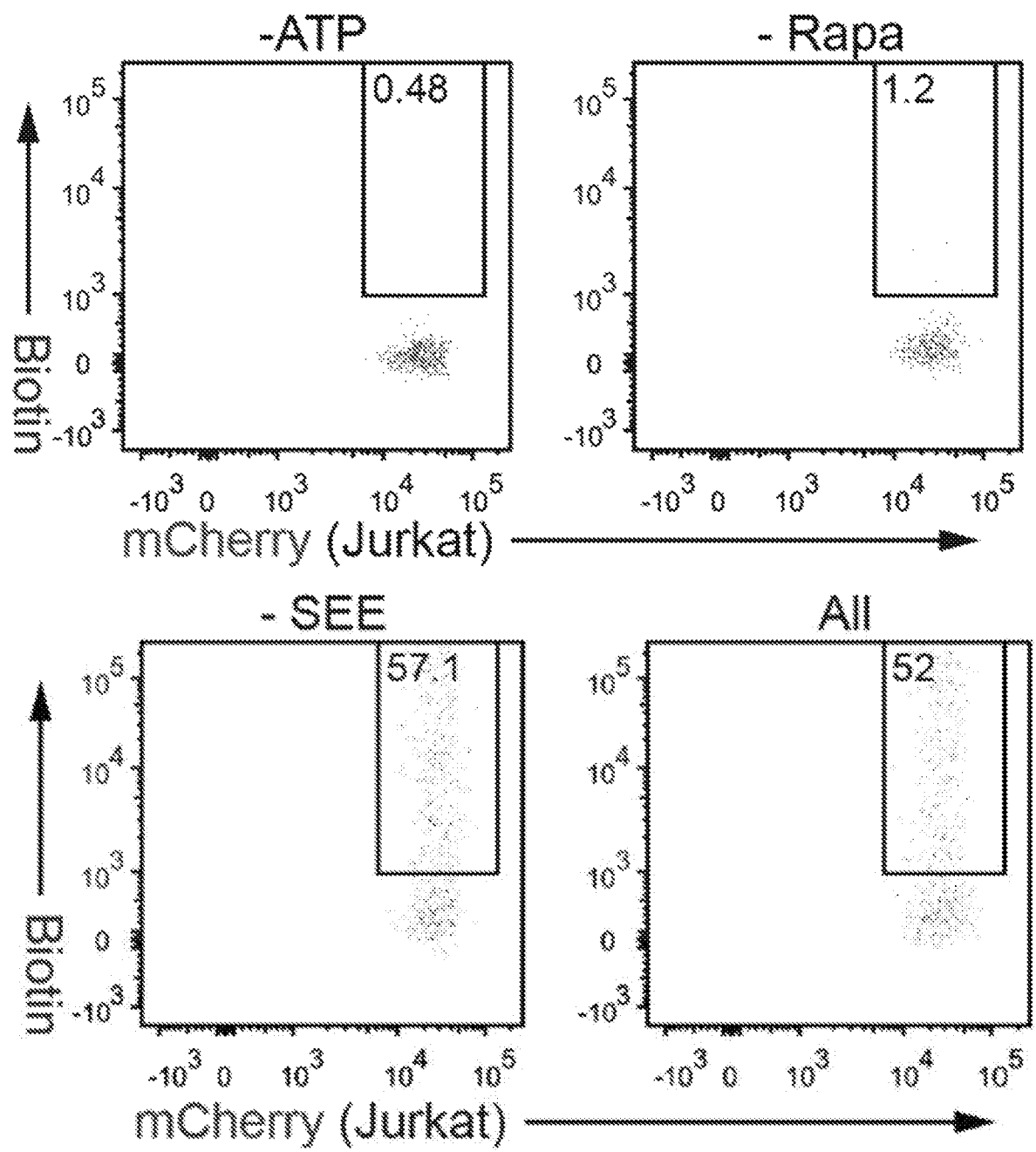
Figure 5E:
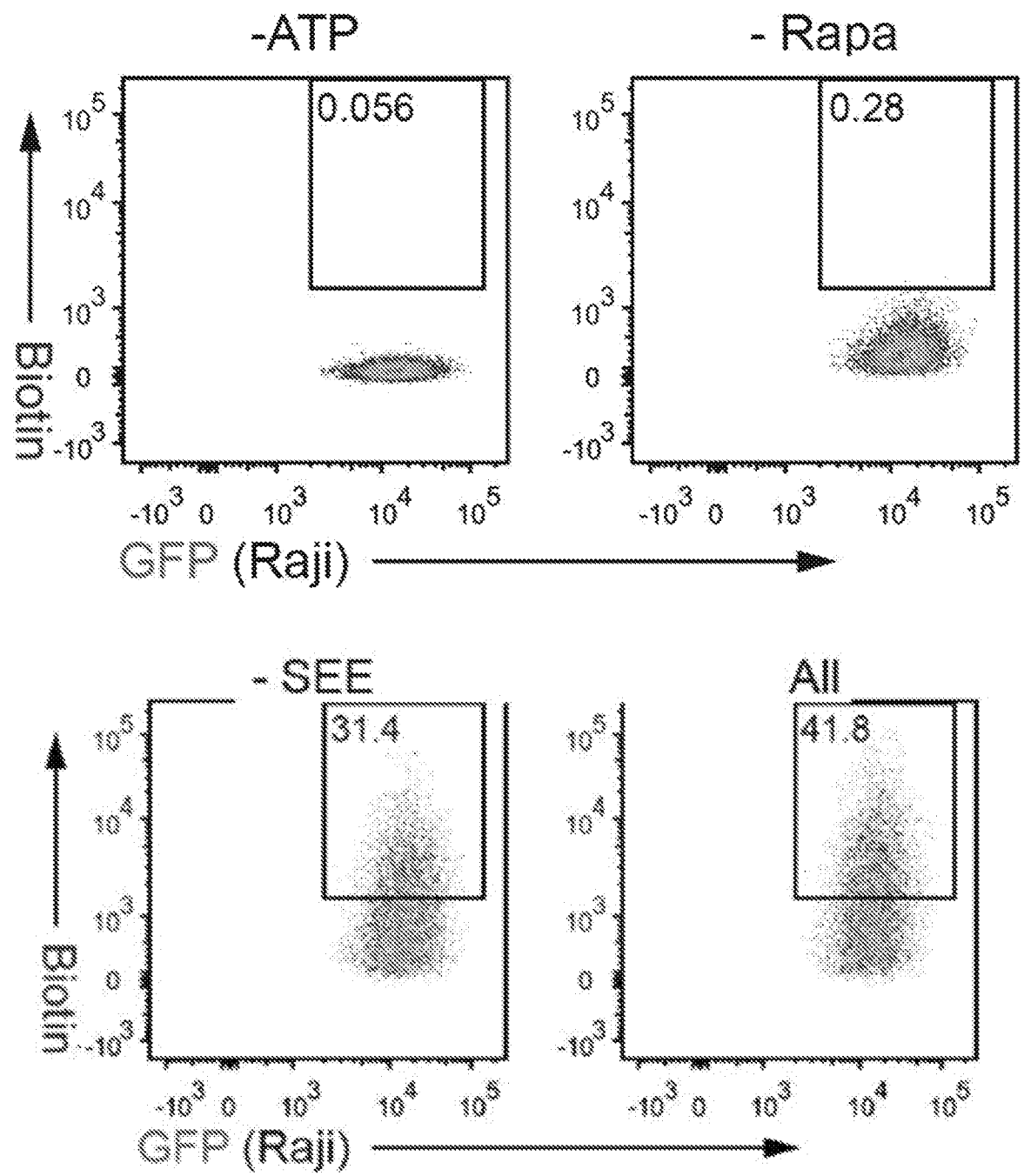

Since CD28 binds to CD86 and CD80 on antigen-presenting cells, we examined if PUP-IT can label Raji B-lymphocyte cells that express CD80 and CD86 on the surface (FIG. 5c). Jurkat cells were transfected with FKBP-CD28, then incubated with FRB-PafA and Raji cells in the presence of rapamycin. While we observed biotin signals on the whole T cell surface, punctate modification sites were observed on Raji cell surface, consistent with partial direct contact between T cells and B cells in a co-culturing condition (FIG. 5d). Flow cytometry analysis further confirmed the labeling of B cells (FIG. 5e). Meanwhile, if we simply co-culture GFP positive T cells with mCherry positive FKBP-CD28 expression T cells, none of the GFP positive cells appear to be labeled with biotin, further indicating that labeling requires direct interaction between two cells.

SEE is an antigen peptide that is required for the engagement of Raji MHC (major histocompatibility complex) and Jurkat TCR (T cell receptor), but it is not required for CD28/CD86(CD80) interaction. The presence of SEE can increase the interaction between Jurkat T cell and Raji B cells. Indeed, with SEE, we observed more labeling of B cells, but the labeling was not dependent on SEE (FIG. 5e). It has been reported that CD28 interacts with CD86/CD80 with low affinity (Kd=4 µM). Our data suggests that weak extracellular protein-protein interactions between CD28 and its ligand alone is enough to trigger Pup-IT labeling, consistent with our observations within the cell.

Identification of Ligand Targeting Cells Using PUP-IT

Figure 6A:
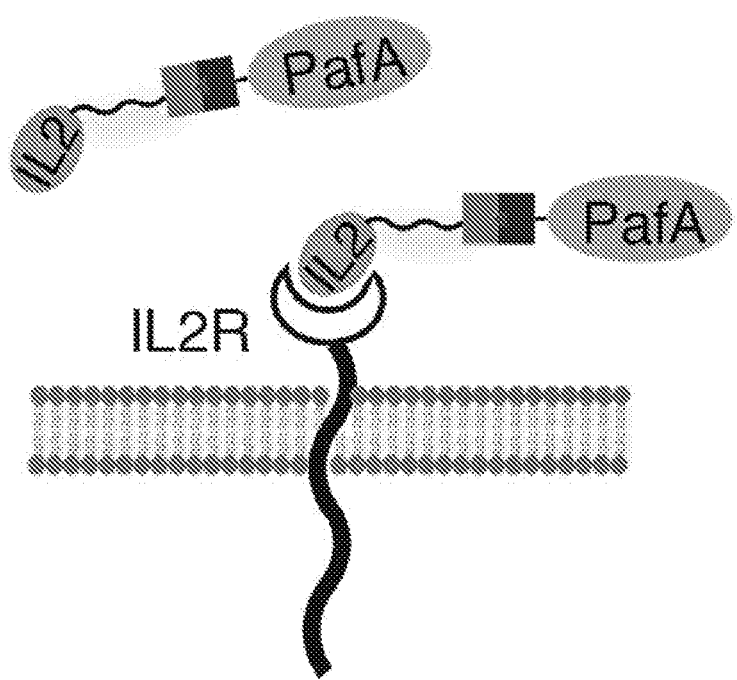
FIG. 6a-d demonstrate that PUP-IT$^{IL2}$ can mediate receptor labeling. (a) Schematic view of th PUP-IT$^{IL2}$ design. PUP-IT$^{FRB}$ is assembled with IL2-FKBP to form PUP-IT$^{IL2}$. (b) Using PUP-IT$^{IL2}$ to label IL2 receptor CD25. Top panel shows CD69 and CD25 expression level as well as background biotin signal in resting T cells. In bottom panel, T cells are treated with anti-CD3 antibody to stimulate IL2 receptor expression before mixed with PUP-IT$^{IL2}$. CD69 and CD25 expression level as well as biotin modification are measured in the activated cells. (c) Cell surface labeling is dependent on both ATP and rapamycin. T cells are first activated then mixed with PUP-IT$^{IL2}$, bio-DE28, ATP and rapamycin. The same reaction was also set up without either ATP or rapamycin. (d) PUP-IT$^{IL2}$ mediated CD25 modification can be inhibited by free IL2. Different amount of free IL2 were added to the PUP-IT$^{IL2}$ reaction with activated Jurkat cells. CD25 expression and biotin signal are measured. Top panel are the representative flow cytometer data from three experimental repeats. Bottom panel are statistics of the decreased cell surface modification with increased free IL2 concentration. Error bars represent SEM.
Figure 6B:
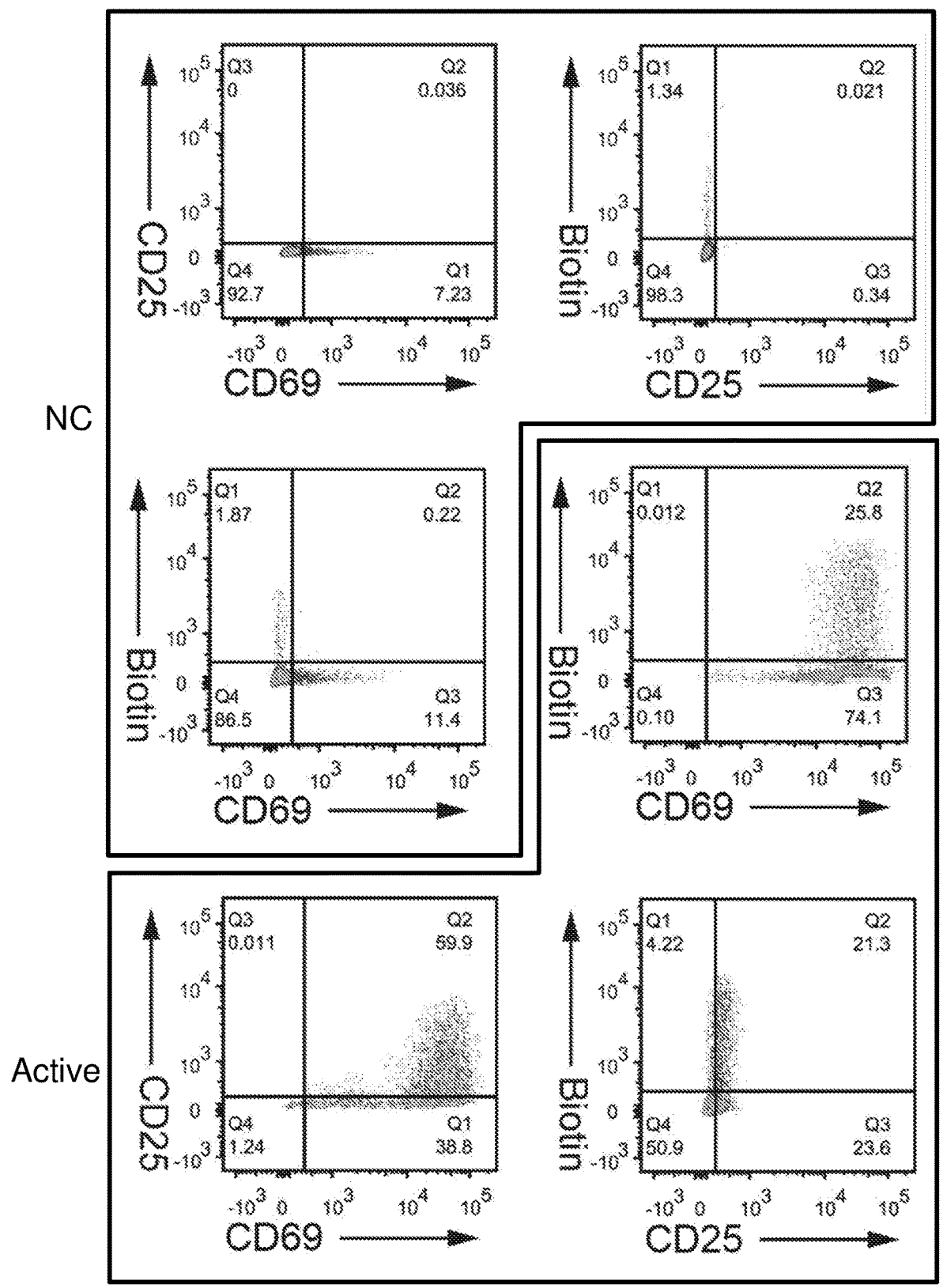
Figure 6C:
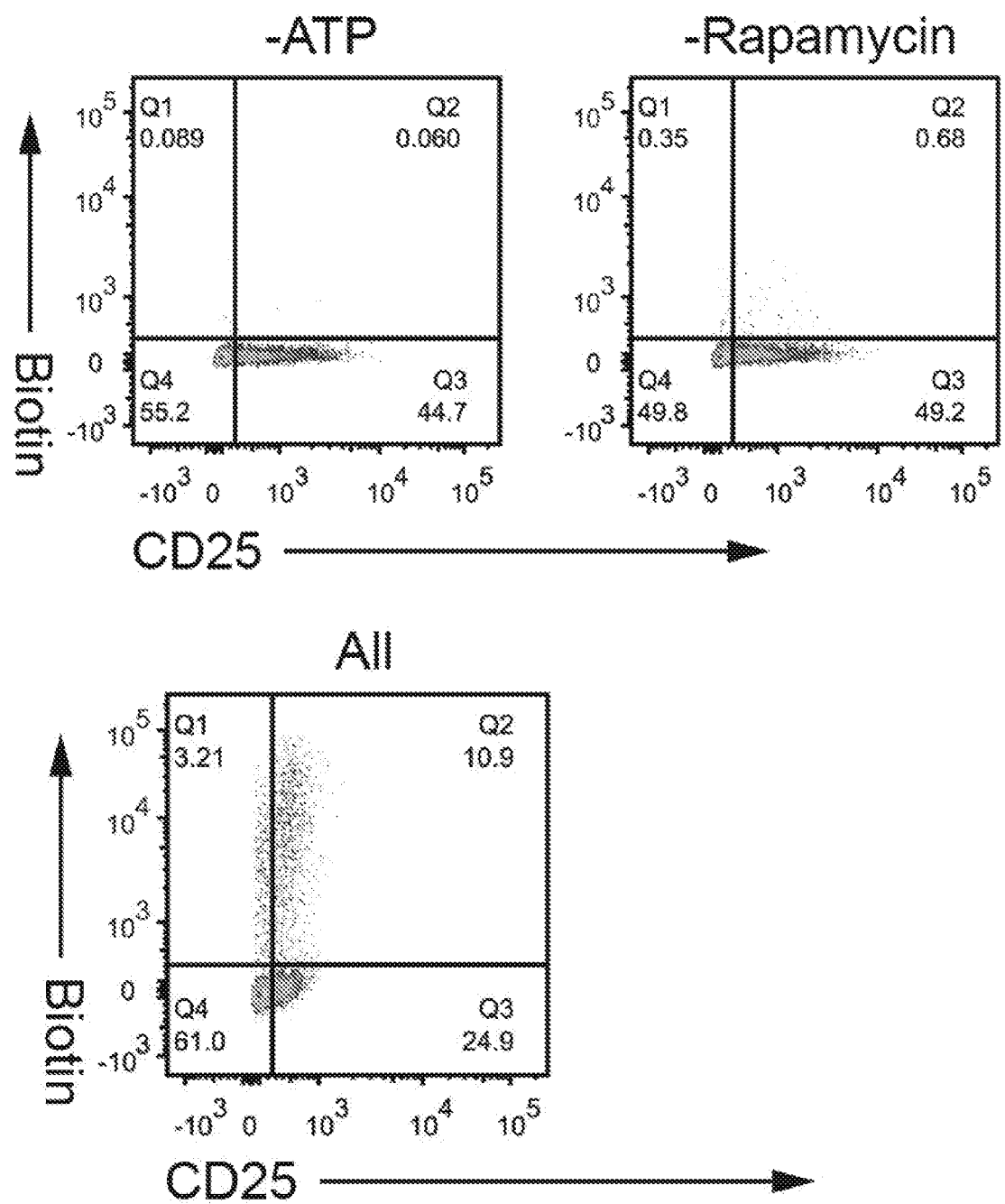

Another technique challenging area is the identification of receptor-ligand pairs. Here we explored the possibility to use PUP-IT to label the receptors when the ligand is known. The model system we studied is the interaction between cytokine IL2 and IL2 receptor subunit CD25. Similar to extracellular PUP-IT$^{CD28}$, we adapted the FKBP-FRB system by purifying IL2-FKBP fusion from mammalian cells and FRB-PafA from bacteria expression system. With the addition of rapamycin, IL2-FKBP/FRB-PafA complex was assembled to mimic IL2-PafA direct fusion (FIG. 6a). T cells normally do not contain detectable CD25 on surface but will upregulate cell surface IL2 receptor CD25 upon activation. We first activated T cells then added IL2-FKBP, FRB-PafA, and bio-DE28 to the cell culture with or without rapamycin. Only the active cells with high CD69, a marker for activated T cells, are labeled with biotin on cell surface (FIG. 6b). Interestingly, those CD25 positive cells disappeared (FIG. 6c). Since we know that the biotin positive cells are active T cells since they are all CD69 positive, it is likely that CD25 got labeled by Pup(E) at lysine sites and such modification blocked CD25 antibody binding. Our results indicate PUP-IT$^{ligand}$ can efficiently label the target receptor with Pup(E).

Figure 6D:
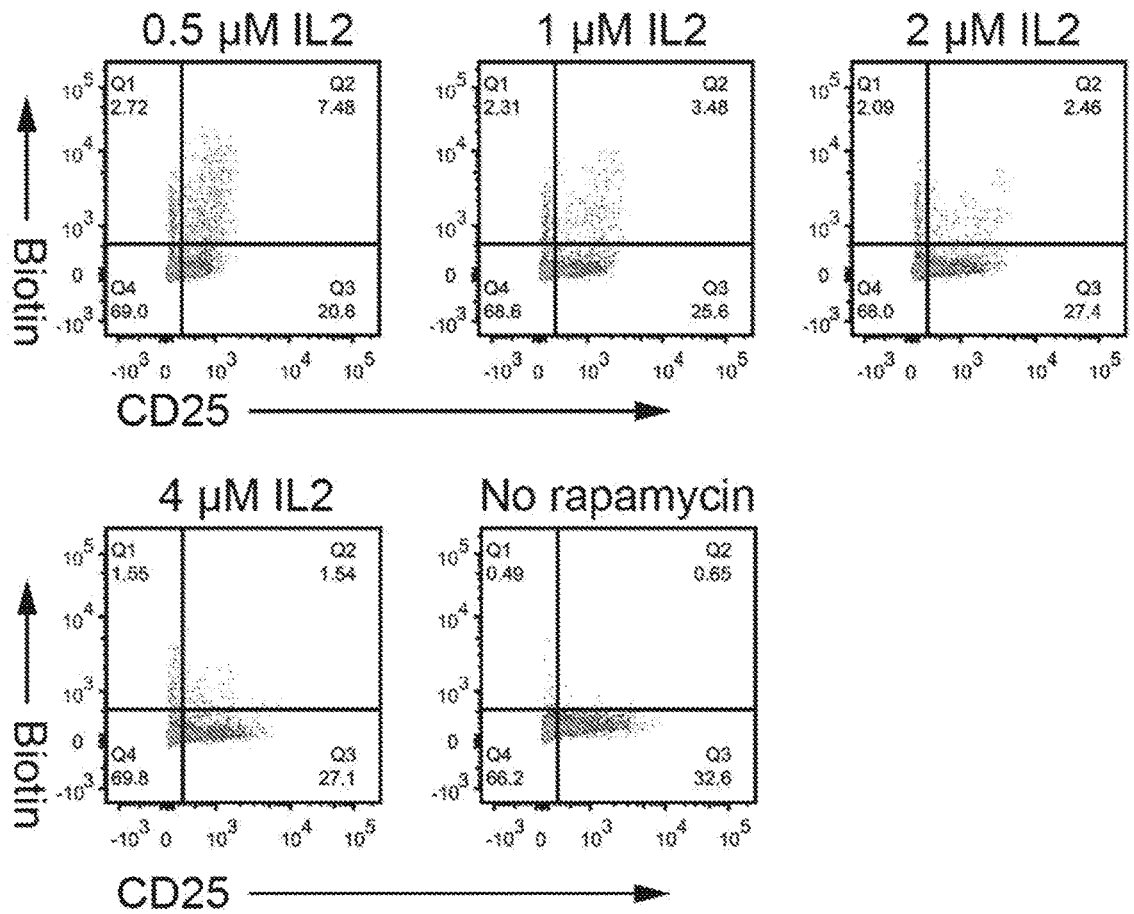
Figure 6D:
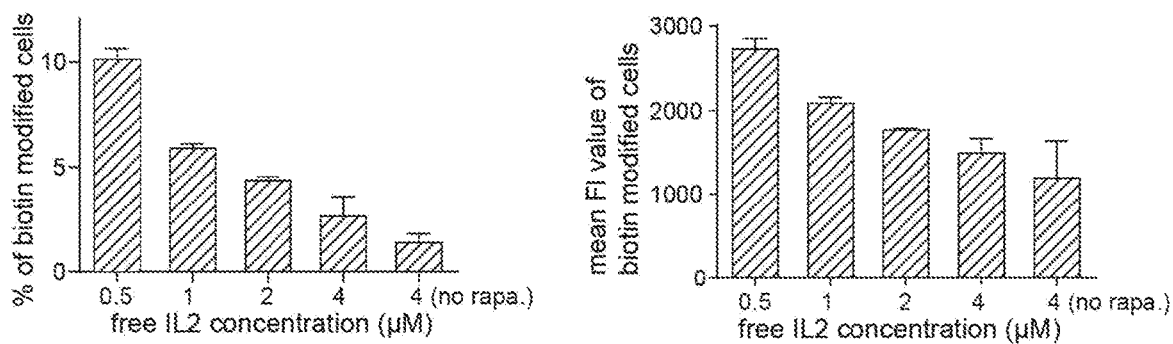

To confirm the cell surface labeling is directly induced by IL2/CD25 interaction, we titrated IL2-FKBP concentration. With more IL2-FKBP, we observe more cell surface modification. Furthermore, we added free IL2 to compete IL2-FKBP for CD25 binding. With increased free IL2, less cell surface modification was detected (FIG. 6d). All together, these results indicate the fusion of PafA to a peptide cytokine can effectively label the corresponding receptor, and potentially can help the identification of novel receptors.

Identification of GTPases That May Mediate Cytoskeleton Remodeling by CD28

CD28 mediated-costimulation is considered to be one of the key mechanisms to maintain peripheral tolerance. Abatacept, a CTLA4-Ig fusion protein that competitively blocks the ability of CD28 to interact with its ligands B7s (extracellular region of CD86/CD80), has been approved for the therapy of rheumatoid arthritis. Therefore, the study of CD28 interactome may help us identify more potential therapeutic target. Our previous study, in which a synthesized CD28 cytoplasmic tail was used to affinity purify CD28-interacting proteins from T cell lysate, identified 28 proteins that bind with CD28 in a phosphorylation-dependent manner. Here we used PUP-IT approach to identify >50 proteins. Some of these proteins, such as LCK, p85 and CSK are revealed in both studies. Proteins that not show in this study may be more dependent on phosphorylation of CD28 to bind.

Previous study suggested one important CD28-mediated function is to regulate actin cytoskeleton remodeling, which intersects with signaling events mediated by TCR. However, it is not clear how CD28 affects the actin dynamics. Interestingly, here we find a significant fraction of CD28-binding proteins are cytoskeleton-remodeling regulators. Small GTPases are key components for cytoskeleton remodeling. We find several small GTPases, such as Cdc42 and RHOA, and other GTPase regulators. IQGAP2 is GTPase-activating Protein (GAP), while ARHGDIB and GDI2 are GDP-dissociation inhibitors (GDIs), which reduce the rate of GDP dissociation from GTPase. In addition, ROCK1 is a downstream effector of small GTPase (RhoA) and DOCK2 is a guanine nucleotide exchange factor (GEF) that activates GTPase. Taken together, these data suggest CD28 might regulate actin dynamics by transiently interacting with multiple small GTPases and their regulators as well as downstream effectors. Further functional validations will be required to dissect the molecular mechanism with or without CD28 signaling.

Versatile Application of PUP-IT

In addition to identify cytosolic interactions, we have shown that PUP-IT functions in the ex vivo environment. With receptor/ligand pairs, we can link PafA to one and the other will get covalently modified. This potentially can be used to identify the ligand for orphan receptors or to identify the receptor for a known cytokine. The extracellular labeling is even cleaner than the cellular reactions since less background proteins are around. Moreover, it is usually challenging to express membrane protein fusions. The PUP-IT$^{FRB}$ we developed will allow the assembly of PafA with different membrane proteins as well as secreted proteins. Thus more membrane proteins can adapt the PUP-IT strategy.

PUP-IT may be used as a general tool for specific protein or cell labeling. Enzymatic labeling of proteins has been used as a powerful tool to study protein chemistry or facilitate fluorescent labeling. Previously, phosphopantetheinyltransferase, sortase, and transglutaminase have been developed as useful tools to site-specifically label proteins and cells[35-38]. We expect PUP-IT may be used in a similar way to specifically label protein lysines. In addition, bio-DE28, a substrate peptide we used for this study, is chemically synthesized and the N-terminal biotin moiety can be easily replaced by fluorophores or any other chemical groups if needed.

Things to Consider for PUP-IT Application

Since Pup(E) stays on enzyme, whether the lysines on substrate get modified dependents on the geometry and orientation between PafA and prey protein. This requires a relative flexible and long linker between PafA and bait to allow the binding prey to be presented at different geometry. For all the PUP-IT design used in this study, there is a 15-20 amino acids linker between PafA and the bait protein. The distance each amino acid can contribute is about 3-4 Å, so a 20 amino acid linker can reach out about 60-80 Å, which is about the average size of a 60 kDa globule protein. However, for future studies of proteins with larger molecule weight, a longer linker should be considered for efficient labeling.

Like most proximity labeling enzymes, the unwanted self-modification is inevitable, same for PUP-IT. Self-modification potentially could inactivate the enzyme, deplete substrates and bring background signals to the mass spectrometry experiments. Therefore, for in cell experiments, we suggest to use an inducible system to limit constitutive self-labeling before the prey proteins are engaged. More precise temporal and local controls will reduce the labeling background.

Compare PUP-IT With Other Method to Identify Membrane Protein Interaction

Identification of membrane protein interacting proteins has long been problematic, partly because of the insolubility of membrane proteins and the disruption of membrane structure. Previously, many methods have been developed, mostly involving the generation of a prey library. Split protein strategies have been used with half of an active enzyme fused to bait while the other half of the enzyme fused to the prey library. Only in the presence of bait-prey interaction can the split enzyme turn active and initiate the detection signal. This method requires the generation of a biased library and the over-expression of prey fusion proteins may disrupt their normal cellular function. PUP-IT only requires the modification on the bait protein that leave the whole proteome as the targeting library, significantly increases the candidate pool.

Compare PUP-IT With Other Proximity Tagging Approaches

In recent years, proximity tagging technology has been developed to mark target protein or organelle with biotin tag in living cells with intact membrane structure and active cellular function. BioID uses a mutated biotin ligase that promiscuously attach biotin to nearby lysines. APEX is an engineered peroxidase that can activate biotin-phenol to attack many different amino acids. NEDDylator is an adapted ubiquitin ligase that hijacks the endogenous NEDDylation pathway to label proteins. Similar to BioID and APEX, PUP-IT is derived from prokaryotic cells, which is orthogonal to endogenous cellular pathways, minimizes the potential risk of interfering with normal cellular events.

PUP-IT system has the potential to be used in animal models. Current tagging methods require the delivery of chemical compounds into cells, which is hard to achieve with animals. By contrast, all components of PUP-IT system can be expressed in cells, thus amendable by genetic approaches. Overall, the PUP-IT system is orthogonal, highly active, with small labeling radius, and less toxic to the cells.

The present disclosure is not to be limited in scope by the specific embodiments described which are intended as single illustrations of individual aspects of the disclosure, and any compositions or methods which are functionally equivalent are within the scope of this disclosure. It will be apparent to those skilled in the art that various modifications and variations can be made in the methods and compositions of the present disclosure without departing from the spirit or scope of the disclosure. Thus, it is intended that the present disclosure cover the modifications and variations of this disclosure provided they come within the scope of the appended claims and their equivalents.

All publications and patent applications mentioned in this specification are herein incorporated by reference to the same extent as if each individual publication or patent application was specifically and individually indicated to be incorporated by reference.

The invention claimed is:

1. A method of detecting binding between a protein having at least a lysine residue and a molecule that interacts with the protein, comprising:
   incubating a sample that comprises (a) a prokaryotic ubiquitin-like protein (Pup), (b) the protein, and (c) the molecule coupled to a Pup ligase, under conditions to allow the protein to bind the molecule, thereby allowing the Pup ligase to conjugate the Pup to the lysine residue of the protein; and
   detecting the conjugation of the Pup to the protein which indicates binding between the protein and the molecule.

2. The method of claim 1, wherein the molecule is a second protein, a small molecule drug, a hormone, a lipid or a polysaccharide.

3. The method of claim 1, wherein the Pup ligase is conjugated to the molecule.

4. The method of claim 1, wherein the Pup ligase is coupled to the molecule through a pair of proteins capable of binding each other.

5. The method of claim 4, wherein the binding is chemically induced dimerization (CID).

6. The method of claim 1, wherein the molecule is a second protein and the Pup ligase is fused to the molecule.

7. The method of claim 1, wherein the binding is through hydrophobic interaction, electro statistic interaction, or hydrogen bond.

8. The method of claim 1, wherein at least one of the protein and the molecule is a membrane-bound or transmembrane protein.

9. The method of claim 1, wherein the protein is present on the surface of a first cell and the molecule is present on a second cell.

10. The method of claim 9, wherein the first cell is a tumor cell and the second cell is a CAR-T cell or vice versa.

11. A method of coupling a molecule to a protein having at least a lysine residue, comprising contacting the protein with (a) the molecule coupled to a prokaryotic ubiquitin-like protein (Pup) in the presence of (b) a Pup ligase coupled to a second protein capable of binding the protein, under conditions to allow the second protein to bind the protein thereby enabling the Pup ligase to conjugate the Pup to the lysine residue, thereby coupling the molecule to the protein.

12. The method of claim 11, wherein the protein is an antibody.

13. The method of claim 11, wherein the second protein is protein G or an antibody having specificity to the Fc fragment of the antibody.

14. The method of claim 11, wherein the molecule is selected from the group consisting of a small molecule drug, a detectable label, a nucleotide, a protein, and combinations thereof.

15. The method of claim 1 where the prokaryotic ubiquitin-like protein (Pup) ligase is coupled to a transmembrane protein.

16. The method of claim 15, wherein the Pup ligase is fused to the intracellular domain of the transmembrane protein.

17. The method of claim 16, wherein the Pup ligase is fewer than 20 amino acid residues away from the intracellular terminus of the protein.

* * * * *

SEQUENCE LISTING

```
<160> NUMBER OF SEQ ID NOS: 15

<210> SEQ ID NO 1
<211> LENGTH: 67
<212> TYPE: PRT
<213> ORGANISM: Artificial Sequence
<220> FEATURE:
<223> OTHER INFORMATION: Synthetic

<400> SEQUENCE: 1

Met Ser Val Val Asn Ala Lys Gln Thr Gln Ile Met Gly Gly Gly Gly
1               5                   10                  15

Arg Asp Glu Asp Asn Thr Glu Asp Ser Ala Gln Ala Ser Gly Gln Val
            20                  25                  30

Gln Ile Asn Thr Glu Gly Val Asp Ser Leu Leu Asp Glu Ile Asp Gly
        35                  40                  45
```

```
Leu Leu Glu Asn Asn Ala Glu Glu Phe Val Arg Ser Tyr Val Gln Lys
 50                  55                  60

Gly Gly Glu
 65

<210> SEQ ID NO 2
<211> LENGTH: 28
<212> TYPE: PRT
<213> ORGANISM: Artificial Sequence
<220> FEATURE:
<223> OTHER INFORMATION: Synthetic

<400> SEQUENCE: 2

Asp Ser Leu Leu Asp Glu Ile Asp Gly Leu Leu Glu Asn Asn Ala Glu
 1               5                  10                  15

Glu Phe Val Arg Ser Tyr Val Gln Lys Gly Gly Glu
             20                  25

<210> SEQ ID NO 3
<211> LENGTH: 63
<212> TYPE: PRT
<213> ORGANISM: Artificial Sequence
<220> FEATURE:
<223> OTHER INFORMATION: Synthetic

<400> SEQUENCE: 3

Met Thr Asn Pro Gln Ser Gln Ile Ser Gly Gly Gly Asp Arg Pro Glu
 1               5                  10                  15

Asp Thr Asn Asp Asp Ala Gln Gly Leu Gly Gln Ala Gln Val Asn Thr
             20                  25                  30

Ala Gly Thr Asp Asp Leu Leu Asp Glu Ile Asp Gly Leu Leu Glu Glu
         35                  40                  45

Asn Ala Glu Glu Phe Val Ser Ser Tyr Val Gln Lys Gly Gly Gln
     50                  55                  60

<210> SEQ ID NO 4
<211> LENGTH: 67
<212> TYPE: PRT
<213> ORGANISM: Artificial Sequence
<220> FEATURE:
<223> OTHER INFORMATION: Synthetic

<400> SEQUENCE: 4

Met Thr Thr Gly Gly Ser Gly Gln Gly Gln Val His Gly Gly Arg Gly
 1               5                  10                  15

Arg Gly Asp Gly Pro Ala Ser Gly Asp Val Thr Ala Ser Gly Gln Glu
             20                  25                  30

Gln Leu Lys Val Ser Gly Thr Asp Asp Leu Leu Asp Glu Ile Asp Gly
         35                  40                  45

Leu Leu Glu Ser Asn Ala Glu Glu Phe Val Lys Ser Tyr Val Gln Lys
     50                  55                  60

Gly Gly Gln
 65

<210> SEQ ID NO 5
<211> LENGTH: 57
<212> TYPE: PRT
<213> ORGANISM: Artificial Sequence
<220> FEATURE:
<223> OTHER INFORMATION: Synthetic

<400> SEQUENCE: 5
```

Met Asn Ala Gly Gly Pro Asn Ala Asp Asp Ser Leu Asp His Ser
1               5                   10                  15

Leu Gly Thr Ala Gln Ala Gln Ile Ser Ala Thr Gly Val Asp Asp Leu
            20                  25                  30

Leu Asp Glu Ile Asp Gly Leu Leu Glu Asn Asn Ala Glu Glu Phe Val
        35                  40                  45

Arg Ser Tyr Val Gln Lys Gly Gly Gln
        50                  55

<210> SEQ ID NO 6
<211> LENGTH: 60
<212> TYPE: PRT
<213> ORGANISM: Artificial Sequence
<220> FEATURE:
<223> OTHER INFORMATION: Synthetic

<400> SEQUENCE: 6

Met Ala Gln Gln Gln Ile His Gly Gly Ser Gly Asn Gly Ser Glu Asp
1               5                   10                  15

Glu Gly Ala Phe Glu Ala Gly Gln Ala Gln Leu Asn Thr Ser Gly Thr
            20                  25                  30

Asp Asp Leu Leu Asp Glu Ile Asp Ala Leu Leu Asp Asn Asn Ala Glu
        35                  40                  45

Glu Phe Val Arg Ser Tyr Val Gln Lys Gly Gly Glu
    50                  55                  60

<210> SEQ ID NO 7
<211> LENGTH: 62
<212> TYPE: PRT
<213> ORGANISM: Artificial Sequence
<220> FEATURE:
<223> OTHER INFORMATION: Synthetic

<400> SEQUENCE: 7

Met Ser Asn Gln Gln Gln Ile His Gly His Thr Gly Gly Gly Asp Asp
1               5                   10                  15

Ala Glu Gly Thr Pro Ala Gln Ala Gly Gln Ala Gln Ile Asn Thr Ala
            20                  25                  30

Gly Thr Asp Asp Leu Leu Asp Glu Ile Asp Ala Leu Leu Asp Thr Asn
        35                  40                  45

Ala Glu Glu Phe Val Arg Ser Phe Val Gln Lys Gly Gly Gln
    50                  55                  60

<210> SEQ ID NO 8
<211> LENGTH: 63
<212> TYPE: PRT
<213> ORGANISM: Artificial Sequence
<220> FEATURE:
<223> OTHER INFORMATION: Synthetic

<400> SEQUENCE: 8

Met Ser Asn Lys Gln Ser Gln Val Gln Gly Ser Gly Ser Gly Asp Asn
1               5                   10                  15

Ser Asp Asp Asp Asp Val Gln Ala Ala Gly Gln Val Gln Ile Asn Thr
            20                  25                  30

Thr Gly Thr Asp Asp Leu Leu Asp Glu Ile Asp Gly Leu Leu Glu Ser
        35                  40                  45

Asn Ala Glu Glu Tyr Val Ser Ser Tyr Val Gln Lys Gly Gly Gln
    50                  55                  60

```
<210> SEQ ID NO 9
<211> LENGTH: 62
<212> TYPE: PRT
<213> ORGANISM: Artificial Sequence
<220> FEATURE:
<223> OTHER INFORMATION: Synthetic

<400> SEQUENCE: 9

Met Ala Asp Lys Gln Val Tyr Ser Ser Gly Lys Gly Pro Thr Asp
1               5                   10                  15

Asp Val Val Asp Gly Gly Ala Gly Gln Val Gln Ile Asn Thr His
            20                  25                  30

Glu Ala Asp Ser Leu Leu Asp Glu Ile Asp Ser Leu Leu Glu Thr Asp
        35                  40                  45

Ser Glu Glu Phe Val Lys Ser Tyr Val Gln Lys Gly Gly Gln
    50                  55                  60

<210> SEQ ID NO 10
<211> LENGTH: 63
<212> TYPE: PRT
<213> ORGANISM: Artificial Sequence
<220> FEATURE:
<223> OTHER INFORMATION: Synthetic

<400> SEQUENCE: 10

Met Ala Gln Asp Gln Ile Asn Ile Ser Gly Gly Gly Asp Asn Gly Glu
1               5                   10                  15

Gly Glu Pro Gly Asp Ala Arg Asn Ala Gly Gln Val Asn Val Asn Thr
            20                  25                  30

Thr Gly Thr Asp Asp Leu Leu Asp Glu Ile Asp Ala Leu Leu Asp Thr
        35                  40                  45

Asn Ala Glu Glu Phe Val Arg Ser Tyr Val Gln Lys Gly Gly Gln
    50                  55                  60

<210> SEQ ID NO 11
<211> LENGTH: 482
<212> TYPE: PRT
<213> ORGANISM: Artificial Sequence
<220> FEATURE:
<223> OTHER INFORMATION: Synthetic

<400> SEQUENCE: 11

Met Ser Thr Val Glu Ser Ala Leu Thr Arg Arg Ile Met Gly Ile Glu
1               5                   10                  15

Thr Glu Tyr Gly Leu Thr Phe Val Asp Gly Asp Ser Lys Lys Leu Arg
            20                  25                  30

Pro Asp Glu Ile Ala Arg Arg Met Phe Arg Pro Ile Val Glu Lys Tyr
        35                  40                  45

Ser Ser Ser Asn Ile Phe Ile Pro Asn Gly Ser Arg Leu Tyr Leu Asp
    50                  55                  60

Val Gly Ser His Pro Glu Tyr Ala Thr Ala Glu Cys Asp Asn Leu Thr
65                  70                  75                  80

Gln Leu Ile Asn Phe Glu Lys Ala Gly Asp Val Ile Ala Asp Arg Met
                85                  90                  95

Ala Val Asp Ala Glu Glu Ser Leu Ala Lys Asp Ile Ala Gly Gln
            100                 105                 110

Val Tyr Leu Phe Lys Asn Asn Val Asp Ser Val Gly Asn Ser Tyr Gly
        115                 120                 125

Cys His Glu Asn Tyr Leu Val Gly Arg Ser Met Pro Leu Lys Ala Leu
    130                 135                 140
```

```
Gly Lys Arg Leu Met Pro Phe Leu Ile Thr Arg Gln Leu Ile Cys Gly
145                 150                 155                 160

Ala Gly Arg Ile His His Pro Asn Pro Leu Asp Lys Gly Glu Ser Phe
                165                 170                 175

Pro Leu Gly Tyr Cys Val Ser Gln Arg Ser Asp His Val Trp Glu Gly
            180                 185                 190

Val Ser Ser Ala Thr Thr Arg Ser Arg Pro Ile Ile Asn Thr Arg Asp
        195                 200                 205

Glu Pro His Ala Asp Ser His Ser Tyr Arg Arg Leu His Val Ile Val
    210                 215                 220

Gly Asp Ala Asn Met Ala Glu Pro Ser Ile Ala Leu Lys Val Gly Ser
225                 230                 235                 240

Thr Leu Leu Val Leu Glu Met Ile Glu Ala Asp Phe Gly Leu Pro Ser
                245                 250                 255

Leu Glu Leu Ala Asn Asp Ile Ala Ser Ile Arg Glu Ile Ser Arg Asp
            260                 265                 270

Ala Thr Gly Ser Thr Leu Leu Ser Leu Lys Asp Gly Thr Thr Met Thr
        275                 280                 285

Ala Leu Gln Ile Gln Gln Val Val Phe Glu His Ala Ser Lys Trp Leu
    290                 295                 300

Glu Gln Arg Pro Glu Pro Glu Phe Ser Gly Thr Ser Asn Thr Glu Met
305                 310                 315                 320

Ala Arg Val Leu Asp Leu Trp Gly Arg Met Leu Lys Ala Ile Glu Ser
                325                 330                 335

Gly Asp Phe Ser Glu Val Asp Thr Glu Ile Asp Trp Val Ile Lys Lys
            340                 345                 350

Lys Leu Ile Asp Arg Phe Ile Gln Arg Gly Asn Leu Gly Leu Asp Asp
        355                 360                 365

Pro Lys Leu Ala Gln Val Asp Leu Thr Tyr His Asp Ile Arg Pro Gly
    370                 375                 380

Arg Gly Leu Phe Ser Val Leu Gln Ser Arg Gly Met Ile Lys Arg Trp
385                 390                 395                 400

Thr Thr Asp Glu Ala Ile Leu Ala Ala Val Asp Thr Ala Pro Asp Thr
                405                 410                 415

Thr Arg Ala His Leu Arg Gly Arg Ile Leu Lys Ala Ala Asp Thr Leu
            420                 425                 430

Gly Val Pro Val Thr Val Asp Trp Met Arg His Lys Val Asn Arg Pro
        435                 440                 445

Glu Pro Gln Ser Val Glu Leu Gly Asp Pro Phe Ser Ala Val Asn Ser
    450                 455                 460

Glu Val Asp Gln Leu Ile Glu Tyr Met Thr Val His Ala Glu Ser Tyr
465                 470                 475                 480

Arg Ser

<210> SEQ ID NO 12
<211> LENGTH: 15
<212> TYPE: PRT
<213> ORGANISM: Artificial Sequence
<220> FEATURE:
<223> OTHER INFORMATION: Synthetic

<400> SEQUENCE: 12

Leu Ala Cys Asp Glu Val Thr Ser Thr Thr Ser Ser Ser Thr Ala
1               5                   10                  15
```

```
<210> SEQ ID NO 13
<211> LENGTH: 15
<212> TYPE: PRT
<213> ORGANISM: Artificial Sequence
<220> FEATURE:
<223> OTHER INFORMATION: Synthetic

<400> SEQUENCE: 13

Thr Leu Phe Pro Asp Val Ser Ser Ser Thr His Pro Tyr His Gly
1               5                   10                  15

<210> SEQ ID NO 14
<211> LENGTH: 15
<212> TYPE: PRT
<213> ORGANISM: Artificial Sequence
<220> FEATURE:
<223> OTHER INFORMATION: Synthetic

<400> SEQUENCE: 14

Ser Glu Leu Asp Ser Pro Ser Ser Thr Ser Ser Ser Ser Gly Ile
1               5                   10                  15

<210> SEQ ID NO 15
<211> LENGTH: 15
<212> TYPE: PRT
<213> ORGANISM: Artificial Sequence
<220> FEATURE:
<223> OTHER INFORMATION: Synthetic

<400> SEQUENCE: 15

Leu Ala Cys Asp Glu Asp Thr Ala Ala Ala Ser Ser Ser Thr Ala
1               5                   10                  15
```